US012642257B2

(12) United States Patent
Suemizu

(10) Patent No.: US 12,642,257 B2
(45) Date of Patent: Jun. 2, 2026

(54) NON-HUMAN VERTEBRATE COMPRISING HUMAN LIVER CELLS TRANSPLANTED THEREIN AND METHOD FOR PRODUCING THE SAME

(71) Applicant: CENTRAL INSTITUTE FOR EXPERIMENTAL ANIMALS, Kawasaki (JP)

(72) Inventor: Hiroshi Suemizu, Kawasaki (JP)

(73) Assignee: Central Institute for Experimental Animals, Kanagawa (JP)

( * ) Notice: Subject to any disclaimer, the term of this patent is extended or adjusted under 35 U.S.C. 154(b) by 715 days.

(21) Appl. No.: 17/049,543

(22) PCT Filed: Dec. 12, 2019

(86) PCT No.: PCT/JP2019/048693
§ 371 (c)(1),
(2) Date: Oct. 21, 2020

(87) PCT Pub. No.: WO2020/122178
PCT Pub. Date: Jun. 18, 2020

(65) Prior Publication Data
US 2021/0251199 A1     Aug. 19, 2021

(30) Foreign Application Priority Data
Dec. 14, 2018     (JP) ................................. 2018-234945

(51) Int. Cl.
*A01K 67/0276*     (2024.01)
*C12N 5/071*      (2010.01)

(52) U.S. Cl.
CPC .......... *A01K 67/0276* (2013.01); *C12N 5/067* (2013.01); *C12N 5/0671* (2013.01); *A01K 2207/12* (2013.01); *A01K 2217/075* (2013.01); *A01K 2227/105* (2013.01); *A01K 2267/035* (2013.01)

(58) Field of Classification Search
CPC ............ C12N 5/067; C12N 2501/2306; A01K 2207/12
See application file for complete search history.

(56) References Cited

FOREIGN PATENT DOCUMENTS

| | | |
|---|---|---|
| JP | 5073836 B2 | 8/2012 |
| JP | 2016-082908 A | 5/2016 |
| WO | WO-2017/070428 A1 | 4/2017 |
| WO | WO-2017/075432 A2 | 5/2017 |

OTHER PUBLICATIONS

Xu et al (Chimeric TK-NOG Mice: A Predictive Model for Cholestatic Human Liver Toxicity. J Pharm & Exp Therapeutics, vol. 352, Feb. 2015) (Year: 2015).*
Britannica information about Vertebrates (Year: 2023).*
Yu et al (A novel humanized mouse model with significant improvement of class-switched, antigen-specific antibody production. Blood, vol. 129, 2017). (Year: 2017).*
Finkelman et al (Anti-Cytokine Antibodies as Carrier Proteins: Prolongation of in Vivo Effects of Exogenous Cytokines by Injection of Cytokine—Anti-Cytokine Antibody Complexes. J of Immuno, vol. 151, 1993) (Year: 1993).*
Bell (Normal Liver Histology 101, Published on American Association for the Study of Liver Diseases on Jun. 2020). (Year: 2020).*
Hasegawa et al (The Reconstituted 'Humanized Liver' in TK-NOG Mice is Mature and Functional. Biochem Biophys Res Commun., vol. 405, 2011; cited in IDS dated Feb. 18, 2022) (Year: 2011).*
Zimmers et al (Massive Liver Growth in Mice Induced by Systemic Interleukin 6 Administration. Hepatology, vol. 38, No. 2, 2003; cited in IDS dated Feb. 18, 2022). (Year: 2003).*
Suematsu et al (Generation of plasmacytomas with the chromosomal translocation t(12;15) in interleukin 6 transgenic mice. PNAS, vol. 89, Jan. 1992) (Year: 1992).*
Mori et al (Generation of a transgenic mouse line for conditional expression of human IL-6. Exp. Anim. 65(4), 455-463, 2016) (Year: 2016).*
Annual Activity Report of Central Institute for Experimental Animals, 61st fiscal year, Apr. 1, 2017 to Mar. 31, 2018, Jul. 2018, pp. 1-65, with partial English translation.
International Search Report dated Mar. 10, 2020 in PCT/JP2019/048693, with English translation.
Ito et al., "Current advances in humanized mouse models," Cellular & Molecular Immunology, 2012, 9:208-214.
Dobrolecki et al., "Patient-derived xenograft (PDX) models in basic and translational breast cancer research," Cancer Metastasis Review, Dec. 27, 2016, 35(4):547-573.
Hasegawa et al., "The reconstituted 'humanized liver' in TK-NOG mice is mature and functional," Biochemical and Biophysical Research Communications, Jan. 14, 2011, 405(3):405-410.
Kallen et al., "The therapeutic potential of interleukin-6 hyperagonists and antagonists," Expert Opinion on Investigational Drugs, Mar. 1997, 6(3):237-266.
Schmidt-Arras et al., "IL-6 pathway in the liver: From physiopathology to therapy," Journal of Hepatology, Feb. 8, 2016, 64(6):1403-1415.
Supplementary European Search Report dated Jan. 5, 2022 in EP 19896323.3.
Zimmers et al., "Massive Liver Growth in Mice Induced by Systemic Interleukin 6 Administration," Hepatology, 2003, 38(2):326-334.
Office Action dated Dec. 16, 2020 in JP 2020-554560.

* cited by examiner

*Primary Examiner* — Emily A Cordas
*Assistant Examiner* — Matasha Dhar
(74) *Attorney, Agent, or Firm* — Foley & Lardner LLP

(57) ABSTRACT

This invention provides a non-human vertebrate exhibiting a higher human liver cell growth rate, a higher human liver cell replacement rate, and higher histological-physiological human reproducibility than existing non-human vertebrates comprising the human liver transplanted therein and a method for producing such non-human vertebrate. Specifically, the method for producing a transgenic non-human vertebrate comprising human liver cells transplanted therein comprises transplanting human liver cells in a non-human vertebrate that has impaired or lowered immune reactions against humans in the presence of human IL-6 in vivo.

10 Claims, 20 Drawing Sheets
Specification includes a Sequence Listing.

Number of weeks after transplantation
(human liver cell LHum17003)

SEQUENCE LISTING

```
<160> NUMBER OF SEQ ID NOS: 4

<210> SEQ ID NO 1
<211> LENGTH: 1131
<212> TYPE: DNA
<213> ORGANISM: Herpes simplex virus
<220> FEATURE:
<221> NAME/KEY: CDS
<222> LOCATION: (1)..(1131)

<400> SEQUENCE: 1 atg gct tcg tac ccc ggc cat caa cac gcg tct gcg ttc gac cag gct        48
Met Ala Ser Tyr Pro Gly His Gln His Ala Ser Ala Phe Asp Gln Ala
1               5                   10                  15 gcg cgt tct cgc ggc cat agc aac cga cgt acg gcg ttg cgc cct cgc        96
Ala Arg Ser Arg Gly His Ser Asn Arg Arg Thr Ala Leu Arg Pro Arg
                20                  25                  30 cgg cag caa gaa gcc acg gaa gtc cgc ccg gag cag aaa atg ccc acg       144
Arg Gln Gln Glu Ala Thr Glu Val Arg Pro Glu Gln Lys Met Pro Thr
            35                  40                  45 cta ctg cgg gtt tat ata gac ggt ccc cac ggg atg ggg aaa acc acc       192
Leu Leu Arg Val Tyr Ile Asp Gly Pro His Gly Met Gly Lys Thr Thr
        50                  55                  60 acc acg caa ctg ctg gtg gcc ctg ggt tcg cgc gac gat atc gtc tac       240
Thr Thr Gln Leu Leu Val Ala Leu Gly Ser Arg Asp Asp Ile Val Tyr
65                  70                  75                  80 gta ccc gag ccg atg act tac tgg cgg gtg ctg ggg gct tcc gag aca       288
Val Pro Glu Pro Met Thr Tyr Trp Arg Val Leu Gly Ala Ser Glu Thr
                85                  90                  95 atc gcg aac atc tac acc aca caa cac cgc ctc gac cag ggt gag ata       336
Ile Ala Asn Ile Tyr Thr Thr Gln His Arg Leu Asp Gln Gly Glu Ile
                100                 105                 110 tcg gcc ggg gac gcg gcg gtg gta atg aca agc gcc cag ata aca atg       384
Ser Ala Gly Asp Ala Ala Val Val Met Thr Ser Ala Gln Ile Thr Met
            115                 120                 125 ggc atg cct tat gcc gtg acc gac gcc gtt ctg gct cct cat atc ggg       432
Gly Met Pro Tyr Ala Val Thr Asp Ala Val Leu Ala Pro His Ile Gly
        130                 135                 140
```

```
ggg gag gct ggg agc tca cat gtc ccg ccc ccg gcc ctc acc att ttg      480
Gly Glu Ala Gly Ser Ser His Val Pro Pro Pro Ala Leu Thr Ile Leu
145                 150                 155                 160 gct gac cgc cat ccc atc gca tat ttc tta tgc tac ccg gcc gcg cgg      528
Ala Asp Arg His Pro Ile Ala Tyr Phe Leu Cys Tyr Pro Ala Ala Arg
                165                 170                 175 tac ctt atg ggc agc atg acc ccc cag gcc gtg ctg gcg ttc gtg gcc      576
Tyr Leu Met Gly Ser Met Thr Pro Gln Ala Val Leu Ala Phe Val Ala
            180                 185                 190 ctc atc ccg ccg acc ttg ccc ggc acc aac atc gtg ctt ggg gcc ctt      624
Leu Ile Pro Pro Thr Leu Pro Gly Thr Asn Ile Val Leu Gly Ala Leu
        195                 200                 205 ccg gag gac aga cac atc gac cgc ctg gcc aaa cgc cag cgc ccc ggc      672
Pro Glu Asp Arg His Ile Asp Arg Leu Ala Lys Arg Gln Arg Pro Gly
        210                 215                 220 gag cgg ctg gac ctg gct atg ctg gct gcg att cgc cgc gtt tac ggg      720
Glu Arg Leu Asp Leu Ala Met Leu Ala Ala Ile Arg Arg Val Tyr Gly
225                 230                 235                 240 cta ctt gcc aat acg gtg cgg tat ctg cag tgc ggc ggg tcg tgg cgg      768
Leu Leu Ala Asn Thr Val Arg Tyr Leu Gln Cys Gly Gly Ser Trp Arg
                245                 250                 255 gag gac tgg gga cag ctt tcg ggg acg gcc gtg ccg ccc cag ggt gcc      816
Glu Asp Trp Gly Gln Leu Ser Gly Thr Ala Val Pro Pro Gln Gly Ala
                260                 265                 270 gag ccc cag agc aac gcg ggc cca cga ccc cat atc ggg gac acg tta      864
Glu Pro Gln Ser Asn Ala Gly Pro Arg Pro His Ile Gly Asp Thr Leu
            275                 280                 285 ttt acc ctg ttt cgg gcc ccc gag ttg ctg gcc ccc aac ggc gac ctg      912
Phe Thr Leu Phe Arg Ala Pro Glu Leu Leu Ala Pro Asn Gly Asp Leu
        290                 295                 300 tat aac gtg ttt gcc tgg gcc ttg gac gtc ttg gcc aaa cgc ctc cgt      960
Tyr Asn Val Phe Ala Trp Ala Leu Asp Val Leu Ala Lys Arg Leu Arg
305                 310                 315                 320 tcc atg cac gtc ttt atc ctg gat tac gac caa tcg ccc gcc ggc tgc     1008
Ser Met His Val Phe Ile Leu Asp Tyr Asp Gln Ser Pro Ala Gly Cys
                325                 330                 335 cgg gac gcc ctg ctg caa ctt acc tcc ggg atg gtc cag acc cac gtc     1056
Arg Asp Ala Leu Leu Gln Leu Thr Ser Gly Met Val Gln Thr His Val
            340                 345                 350 acc acc ccc ggc tcc ata ccg acg ata tgc gac ctg gcg cgc acg ttt     1104
Thr Thr Pro Gly Ser Ile Pro Thr Ile Cys Asp Leu Ala Arg Thr Phe
            355                 360                 365 gcc cgg gag atg ggg gag gct aac tga                                  1131
Ala Arg Glu Met Gly Glu Ala Asn
        370                 375
```

<210> SEQ ID NO 2
<211> LENGTH: 376
<212> TYPE: PRT
<213> ORGANISM: Herpes simplex virus

<400> SEQUENCE: 2

```
Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Pro Glu Gln Lys Met Pro Thr
        35                  40                  45

Leu Leu Arg Val Tyr Ile Asp Gly Pro His Gly Met Gly Lys Thr Thr
```

-continued

```
            50                  55                  60
Thr Thr Gln Leu Leu Val Ala Leu Gly Ser Arg Asp Asp Ile Val Tyr
65                  70                  75                  80

Val Pro Glu Pro Met Thr Tyr Trp Arg Val Leu Gly Ala Ser Glu Thr
                85                  90                  95

Ile Ala Asn Ile Tyr Thr Thr Gln His Arg Leu Asp Gln Gly Glu Ile
                100                 105                 110

Ser Ala Gly Asp Ala Ala Val Val Met Thr Ser Ala Gln Ile Thr Met
            115                 120                 125

Gly Met Pro Tyr Ala Val Thr Asp Ala Val Leu Ala Pro His Ile Gly
        130                 135                 140

Gly Glu Ala Gly Ser Ser His Val Pro Pro Ala Leu Thr Ile Leu
145                 150                 155                 160

Ala Asp Arg His Pro Ile Ala Tyr Phe Leu Cys Tyr Pro Ala Ala Arg
                165                 170                 175

Tyr Leu Met Gly Ser Met Thr Pro Gln Ala Val Leu Ala Phe Val Ala
                180                 185                 190

Leu Ile Pro Pro Thr Leu Pro Gly Thr Asn Ile Val Leu Gly Ala Leu
            195                 200                 205

Pro Glu Asp Arg His Ile Asp Arg Leu Ala Lys Arg Gln Arg Pro Gly
        210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
                260                 265                 270

Glu Pro Gln Ser Asn Ala Gly Pro Arg Pro His Ile Gly Asp Thr Leu
            275                 280                 285

Phe Thr Leu Phe Arg Ala Pro Glu Leu Leu Ala Pro Asn Gly Asp Leu
        290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
            355                 360                 365

Ala Arg Glu Met Gly Glu Ala Asn
        370                 375
```

```
<210> SEQ ID NO 3
<211> LENGTH: 1131
<212> TYPE: DNA
<213> ORGANISM: Herpes simplex virus
<220> FEATURE:
<221> NAME/KEY: CDS
<222> LOCATION: (1)..(1131)

<400> SEQUENCE: 3 atg gct tcg tac ccc tgc cat caa cac gcg tct gcg ttc gac cag gct      48
Met Ala Ser Tyr Pro Cys His Gln His Ala Ser Ala Phe Asp Gln Ala
1               5                   10                  15 gcg cgt tct cgc ggc cat agc aac cga cgt acg gcg ttg cgc cct cgc      96
Ala Arg Ser Arg Gly His Ser Asn Arg Arg Thr Ala Leu Arg Pro Arg
```

```
                    20                  25                  30 cgg cag caa gaa gcc acg gaa gtc cgc ctg gag cag aaa atg ccc acg      144
Arg Gln Gln Glu Ala Thr Glu Val Arg Leu Glu Gln Lys Met Pro Thr
        35                  40                  45 cta ctg cgg gtt tat ata gac ggt cct cac ggg atg ggg aaa acc acc      192
Leu Leu Arg Val Tyr Ile Asp Gly Pro His Gly Met Gly Lys Thr Thr
        50                  55                  60 acc acg caa ctg ctg gtg gcc ctg ggt tcg cgc gac gat atc gtc tac      240
Thr Thr Gln Leu Leu Val Ala Leu Gly Ser Arg Asp Asp Ile Val Tyr
65                  70                  75                  80 gta ccc gag ccg atg act tac tgg cag gtg ctg ggg gct tcc gag aca      288
Val Pro Glu Pro Met Thr Tyr Trp Gln Val Leu Gly Ala Ser Glu Thr
                    85                  90                  95 atc gcg aac atc tac acc aca caa cac cgc ctc gac cag ggt gag ata      336
Ile Ala Asn Ile Tyr Thr Thr Gln His Arg Leu Asp Gln Gly Glu Ile
                100                 105                 110 tcg gcc ggg gac gcg gcg gtg gta atg aca agc gcc cag ata aca atg      384
Ser Ala Gly Asp Ala Ala Val Val Met Thr Ser Ala Gln Ile Thr Met
            115                 120                 125 ggc atg cct tat gcc gtg acc gac gcc gtt ctg gct cct cat atc ggg      432
Gly Met Pro Tyr Ala Val Thr Asp Ala Val Leu Ala Pro His Ile Gly
        130                 135                 140 ggg gag gct ggg agc tca cat gcc ccg ccc ccg gcc ctc acc ctc atc      480
Gly Glu Ala Gly Ser Ser His Ala Pro Pro Pro Ala Leu Thr Leu Ile
145                 150                 155                 160 ttc gac cgc cat ccc atc gcc gcc ctc ctg tgc tac ccg gcc gcg cga      528
Phe Asp Arg His Pro Ile Ala Ala Leu Leu Cys Tyr Pro Ala Ala Arg
                165                 170                 175 tac ctt atg ggc agc atg acc ccc cag gcc gtg ctg gcg ttc gtg gcc      576
Tyr Leu Met Gly Ser Met Thr Pro Gln Ala Val Leu Ala Phe Val Ala
            180                 185                 190 ctc atc ccg ccg acc ttg ccc ggc aca aac atc gtg ttg ggg gcc ctt      624
Leu Ile Pro Pro Thr Leu Pro Gly Thr Asn Ile Val Leu Gly Ala Leu
        195                 200                 205 ccg gag gac aga cac atc gac cgc ctg gcc aaa cgc cag cgc ccc ggc      672
Pro Glu Asp Arg His Ile Asp Arg Leu Ala Lys Arg Gln Arg Pro Gly
    210                 215                 220 gag cgg ctt gac ctg gct atg ctg gcc gcg att cgc cgc gtt tac ggg      720
Glu Arg Leu Asp Leu Ala Met Leu Ala Ala Ile Arg Arg Val Tyr Gly
225                 230                 235                 240 ctg ctt gcc aat acg gtg cgg tat ctg cag ggc ggc ggg tcg tgg cgg      768
Leu Leu Ala Asn Thr Val Arg Tyr Leu Gln Gly Gly Gly Ser Trp Arg
                245                 250                 255 gag gat tgg gga cag ctt tcg ggg acg gcc gtg ccg ccc cag ggt gcc      816
Glu Asp Trp Gly Gln Leu Ser Gly Thr Ala Val Pro Pro Gln Gly Ala
            260                 265                 270 gag ccc cag agc aac gcg ggc cca cga ccc cat atc ggg gac acg tta      864
Glu Pro Gln Ser Asn Ala Gly Pro Arg Pro His Ile Gly Asp Thr Leu
        275                 280                 285 ttt acc ctg ttt cgg gcc ccc gag ttg ctg gcc ccc aac ggc gac ctg      912
Phe Thr Leu Phe Arg Ala Pro Glu Leu Leu Ala Pro Asn Gly Asp Leu
        290                 295                 300 tac aac gtg ttt gcc tgg gcc ttg gac gtc ttg gcc aaa cgc ctc cgt      960
Tyr Asn Val Phe Ala Trp Ala Leu Asp Val Leu Ala Lys Arg Leu Arg
305                 310                 315                 320 ccc atg cac gtc ttt atc ctg gat tac gac caa tcg ccc gcc ggc tgc     1008
Pro Met His Val Phe Ile Leu Asp Tyr Asp Gln Ser Pro Ala Gly Cys
                325                 330                 335 cgg gac gcc ctg ctg caa ctt acc tcc ggg atg gtc cag acc cac gtc     1056
```

```
Arg Asp Ala Leu Leu Gln Leu Thr Ser Gly Met Val Gln Thr His Val
        340             345             350 acc acc ccc ggc tcc ata ccg acg atc tgc gac ctg gcg cgc acg ttt      1104
Thr Thr Pro Gly Ser Ile Pro Thr Ile Cys Asp Leu Ala Arg Thr Phe
        355             360             365 gcc cgg gag atg ggg gag gct aac tga                                  1131
Ala Arg Glu Met Gly Glu Ala Asn
        370             375
```

<210> SEQ ID NO 4
<211> LENGTH: 376
<212> TYPE: PRT
<213> ORGANISM: Herpes simplex virus

<400> SEQUENCE: 4

```
Met Ala Ser Tyr Pro Cys His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Gly Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320
```

-continued

```
Pro Met His Val Phe Ile Leu Asp Tyr Asp Gln Ser Pro Ala Gly Cys
            325               330               335

Arg Asp Ala Leu Leu Gln Leu Thr Ser Gly Met Val Gln Thr His Val
            340               345               350

Thr Thr Pro Gly Ser Ile Pro Thr Ile Cys Asp Leu Ala Arg Thr Phe
        355               360               365

Ala Arg Glu Met Gly Glu Ala Asn
    370               375
```

NON-HUMAN VERTEBRATE COMPRISING HUMAN LIVER CELLS TRANSPLANTED THEREIN AND METHOD FOR PRODUCING THE SAME

CROSS-REFERENCE TO RELATED APPLICATIONS

This application is the U.S. National Stage of PCT/JP2019/048693, filed Dec. 12, 2019, which claims priority to JP 2018-234945, filed Dec. 14, 2018.

The instant application contains a Sequence Listing which has been submitted in ASCII format via EFS-WEB and is hereby incorporated by reference in its entirety. Said ASCII copy, created on Oct. 19, 2020, is named sequence.txt and is 18,182 bytes.

TECHNICAL FIELD

The present invention relates to a non-human vertebrate comprising human liver cells transplanted therein.

BACKGROUND ART

In the aim of analysis of human-specific hepatitis virus infection, the metabolism of drugs administered or the growth of the human liver, several groups have heretofore produced immune-tolerant mice carrying human liver cells. In mice that carry the foreign thymidine kinase genes in an expressible manner specifically in the liver and comprise human liver cells transplanted therein, in particular, the mouse liver cells had been satisfactorily replaced with human liver cells (a human liver cell replacement rate of approximately 80%) (Patent Literature 1).

CITATION LIST

Patent Literature

[Patent Literature 1] JP Patent No. 5,073,836

SUMMARY OF INVENTION

Technical Problem

The present invention provides a non-human vertebrate exhibiting a higher human liver cell growth rate, a higher human liver cell replacement rate, and higher histological-physiological human reproducibility than existing non-human vertebrates comprising the human liver transplanted therein and a method for producing such non-human vertebrate. Also, the present invention provides a non-human vertebrate that has more effectively reproduced structure and physiology of the human liver tissue and a method for producing such non-human vertebrate.

Solution to Problem

The present inventors have conducted concentrated studies concerning a method for producing mice comprising human liver cells transplanted therein that exhibit a higher human liver cell growth rate and a higher human liver cell replacement rate than existing mice comprising the human liver transplanted therein.

The present inventors discovered that mice comprising human liver cells transplanted therein that would exhibit a high human liver cell growth rate and a high human liver cell replacement rate could be produced in the presence of human IL-6 when transplanting human liver cells into immunodeficient mice. In addition, they discovered that such mouse models exhibiting a high human liver cell growth rate and a high human liver cell replacement rate would have the liver that is very similar to the human liver in which human liver tissue has been efficiently reproduced histologically and physiologically. This has led to the completion of the present invention.

Specifically, the present invention is as follows.

[1] A method for producing a transgenic non-human vertebrate comprising human liver cells transplanted therein comprising transplanting human liver cells into a non-human vertebrate that has impaired or lowered immune reactions against humans in the presence of human IL-6 in vivo.

[2] The method according to [1], wherein the non-human vertebrate that has impaired or lowered immune reactions against humans is an immunodeficient animal.

[3] The method according to [1] or [2], wherein the non-human vertebrate that has impaired or lowered immune reactions against humans is induced to have liver injury in the liver and the human liver cells transplanted in the liver of the non-human vertebrate are allowed to be engrafted therein instead of the liver cells of the non-human vertebrate.

[4] The method according to [3], wherein the liver injury is induced by any of the methods described below:

(i) a method of liver injury induction in the liver of a non-human vertebrate that has impaired or lowered immune reactions against humans and carries the thymidine kinase gene in an expressible manner by administering human liver cells and suicide substrates to the non-human vertebrate;

(ii) a method of liver injury induction in the liver of a non-human vertebrate that has impaired or lowered immune reactions against humans by allowing the urokinase-type plasminogen activator gene to be carried in an expressible manner therein;

(iii) a method of liver injury induction by impairing the fumarylacetoacetate hydrolase (Fah) gene of the non-human vertebrate that has impaired or lowered immune reactions against humans;

(iv) a method of liver injury induction by administering any of the compounds (a) to (e) below:

(a) carbon tetrachloride;

(b) acetaminophen;

(c) d-galactosamine;

(d) thioacetamide; and (e) anti-Fas antibody; and (v) a method involving the use of 2, 3, or 4 of the methods (i) to (iv) above.

[5] The method according to [4], wherein liver injury is induced in the liver of a non-human vertebrate that has impaired or lowered immune reactions against humans and carries the thymidine kinase gene in an expressible manner by administering human liver cells and suicide substrates to the non-human vertebrate.

[6] The method according to any of [1] to [5], wherein the human IL-6 gene is introduced into a non-human vertebrate and expressed therein to allow human IL-6 to be present in vivo.

[7] The method according to any of [1] to [5], wherein human IL-6 is administered to a non-human vertebrate to allow human IL-6 to be present in vivo.

[8] The method according to any of [1] to [5], wherein cultured cells expressing the human IL-6 gene or vector molecules expressing the human IL-6 gene are administered to a non-human vertebrate and expressed therein to allow human IL-6 to be present in vivo.

[9] The method according to any of [4] to [8], wherein the non-human vertebrate is a TK-NOG mouse prepared by:
  (i) a step of microinjecting the human herpes simplex virus type 1-thymidine kinase (HSV-tk) gene into a fertilized egg of a NOD/Shi mouse; and
  (ii) a step of subjecting the NOD/Shi mouse having the human herpes simplex virus type 1-thymidine kinase (HSV-tk) gene obtained in the step (i) to mating with a NOG (NOD/SCID/$\gamma c^{null}$) mouse.

[10] The method according to [9], wherein the TK-NOG mouse is a mouse represented by a gene symbol selected from the group of gene symbols consisting of: NOD.Cg-Prkdc$^{scid}$Il2rg$^{tm1Sug}$Tg (Alb-UL23)7-2/ShiJic, NOD.Cg-Prkdc$^{scid}$Il2rg$^{tm1Sug}$Tg (Ttr-UL23 mutant 30)4-9/ShiJic, and NOD.Cg-Prkdc$^{scid}$Il2rg$^{tm1Suh}$Tg (Ttr-UL23 mutant 30)5-2/ShiJic mice; and NOD.Cg-Prkdc$^{scid}$Il2rg$^{tm1Sug}$Tg (Ttr-UL23 mutant 30)10-15/ShiJic mice.

[11] The method according to [9] or [10], which comprises a step of administering suicide substrates and liver cells isolated from a human to the TK-NOG mouse according to [9] or [10] comprising human IL-6 in vivo, damaging mouse liver cells, and replacing mouse liver cells with human liver cells.

[12] The method according to [9] or [10], wherein the TK-NOG mouse according to [9] or [10] comprising human IL-6 in vivo is a TK-NOG-IL-6 mouse obtained by:
  (i) a step of microinjecting a DNA fragment comprising human IL-6 cDNA into a fertilized egg obtained by mating a female NOD mouse and a male NOG mouse to obtain a human IL-6 transgenic founder mouse;
  (ii) a step of mating the human IL-6 transgenic founder mouse with a NOG mouse to obtain a scid-IL2Rg$^{null}$ mutant; and
  (iii) a step of mating the NOG-IL-6 mouse obtained in step (ii) with a TK-NOG mouse.

[13] The method according to [12], wherein the TK-NOG-IL-6 mouse is represented by a gene symbol selected from the group of gene symbols consisting of N NOD.Cg-Prkdc$^{scid}$Il2rg$^{tm1sug}$ Tg ((Alb-UL23)7-2, CMV-IL-6)/ShiJic, NOD.Cg-Prkdc$^{scid}$Il2rg$^{tm1Sug}$Tg (Ttr-UL23 mutant 30)4-9, CMV-IL-6/ShiJic, NOD.Cg-Prkdc$^{scid}$Il2$^{tm1Sug}$Tg (Ttr-UL23 mutant 30)5-2, CMV-IL-6/ShiJic and NOD.Cg-Prkdc$^{scid}$Il2rg$^{tm1sug}$Tg (Ttr-UL23 mutant 30)10-15, and CMV-IL-6/ShiJic.

[14] The method according to any of [4] to [13], wherein the suicide substrate is a substance that is metabolized into a toxic substance with the aid of thymidine kinase

[15] The method according to [14], wherein the substance that is metabolized into a toxic substance is aciclovir or ganciclovir.

[16] The method according to any of [1] to [15], wherein the human liver cell is a human liver cell line.

[17] The method according to [16], wherein the human liver cell line is HepG2, Hep3B, or HuH-7.

[18] The method according to any of [1] to [15], wherein the human liver cell is a primary human hepatocyte.

[19] The method according to any of [4] to [18], wherein the human herpes simplex virus type 1-thymidine kinase (HSV-tk) gene is positioned under the control of an albumin promoter, a transthyretin promoter, a thyroxine binding globulin promoter, an LST-1 promoter, an α-fetoprotein promoter, or an α-TTP promoter, so that the human herpes simplex virus type 1-thymidine kinase (HSV-tk) gene is carried in an expressible manner specifically in the liver.

[20] A mouse comprising human liver cells transplanted therein, wherein 90% or more mouse liver cells are replaced with human liver cells, a human liver is reproduced, the reproduced liver has a three-dimensional structure and functions of the human liver, and human IL-6 is present in vivo.

[21] The mouse according to [20], wherein the mouse liver cells are damaged by any of the methods described below:
  (i) a method of liver injury induction in the liver of a non-human vertebrate that has impaired or lowered immune reactions against humans and carries the thymidine kinase gene in an expressible manner by administering human liver cells and suicide substrates to the non-human vertebrate;
  (ii) a method of liver injury induction in the liver of a non-human vertebrate that has impaired or lowered immune reactions against humans by allowing the urokinase-type plasminogen activator gene to be carried in an expressible manner therein;
  (iii) a method of liver injury induction by impairing the fumarylacetoacetate hydrolase (Fah) gene of the non-human vertebrate that has impaired or lowered immune reactions against humans;
  (iv) a method of liver injury induction by administering any of the compounds (a) to (e) below:
    (a) carbon tetrachloride;
    (b) acetaminophen;
    (c) d-galactosamine;
    (d) thioacetamide; and
    (e) anti-Fas antibody; and
  (v) a method involving the use of 2, 3, or 4 of the methods (i) to (iv) above.

[22] The mouse comprising human liver cells transplanted therein according to [21], wherein the human herpes simplex virus type 1-thymidine kinase (HSV-tk) gene is carried in an expressible manner specifically in the liver, 90% or more mouse liver cells are replaced with human liver cells, a human liver is reproduced, the reproduced liver has a three-dimensional structure and functions of the human liver, and human IL-6 is present in vivo.

[23] The mouse according to any of [20] to [22], wherein the hepatobiliary tract system of the human liver is constructed, the structure of the functional lobule of the human liver is present, and the hepatic excretory function of foreign bodies normally works.

[24] The mouse according to [22] or [23], which is a mouse (NOD.Cg-Prkdc$^{scid}$Il2rg$^{tm1Sug}$ Tg ((Alb-UL23)7-2, CMV-IL-6)/ShiJic) prepared by:
  (i) a step of microinjecting the human herpes simplex virus type 1-thymidine kinase (HSV-tk) gene into a fertilized egg of a NOD/Shi mouse;
  (ii) a step of subjecting the NOD/Shi mouse having the human herpes simplex virus type 1-thymidine kinase (HSV-tk) gene obtained in the step (i) to mating with a NOG (NOD/SCID/$\gamma c^{null}$) mouse to obtain a NOD.Cg-Prkdc$^{scid}$Il2rg$^{tm1Sug}$Tg (Alb-UL23)7-2/ShiJic mouse;
  (iii) a step of microinjecting a DNA fragment comprising human IL-6 cDNA into a fertilized egg obtained by mating a female NOD mouse and a male NOG mouse to obtain a human IL-6 transgenic founder mouse; and
  (iv) a step of mating the NOG-IL-6 mouse obtained by the step of mating the human IL-6 transgenic founder mouse with a NOG mouse to obtain the scid-IL2Rg$^{null}$ mutant with the mouse obtained in (ii).

[25] The mouse comprising human liver cells transplanted therein according to any of [20] to [24], wherein the human liver cell is a human liver cell line.

[26] The mouse comprising human liver cells transplanted therein according to [25], wherein the human liver cell line is HepG2, Hep3B, or HuH-7.

[27] The mouse comprising human liver cells transplanted therein according to any of [20] to [24], wherein the human liver cell is a primary human hepatocyte.

[28] The mouse comprising human liver cells transplanted therein according to any of [20] to [27], wherein the human herpes simplex virus type 1-thymidine kinase (HSV-tk) gene is positioned under the control of an albumin promoter, a transthyretin promoter, a thyroxine binding globulin promoter, an LST-1 promoter, an α-fetoprotein promoter, or an α-TTP promoter, so that the human herpes simplex virus type 1-thymidine kinase (HSV-tk) gene is carried in an expressible manner specifically in the liver.

[29] The mouse comprising human liver cells transplanted therein according to any of [20] to [28], wherein the uroki-nase-type plasminogen activator gene is further carried in an expressible manner specifically in the liver.

[30] The method according to any of [1] to [19], wherein the growth rate of the transplanted human liver cells is higher by at least 1.5 times, compared with the case in which human IL-6 is not present in vivo.

[31] The method according to any of [1] to [19], which further comprises administering the human anti-IL-6 antibody, following transplantation of human liver cells.

This description includes part or all of the content as disclosed in the description and/or drawings of Japanese Patent Application No. 2018-234945, which is a priority document of the present application.

Advantageous Effects of the Invention

Human liver cells are transplanted into a non-human vertebrate that has impaired or lowered immune reactions against humans in the presence of human IL-6, so that a non-human vertebrate comprising human liver cells transplanted therein that exhibits a high human liver cell growth rate and a high human liver cell replacement rate can be produced.

This demonstrates that human IL-6 has effects of significantly accelerating the growth of human liver cells transplanted in vivo and human IL-6 is useful for the growth of human liver cells in the body of animals other than humans. Animals that carry human liver cells thus produced are useful for not only research of drug metabolism or the liver but also useful as liver cell resources to be provided for in vitro research involving the use of human liver cells.

DESCRIPTION OF EMBODIMENTS

Figure 1:
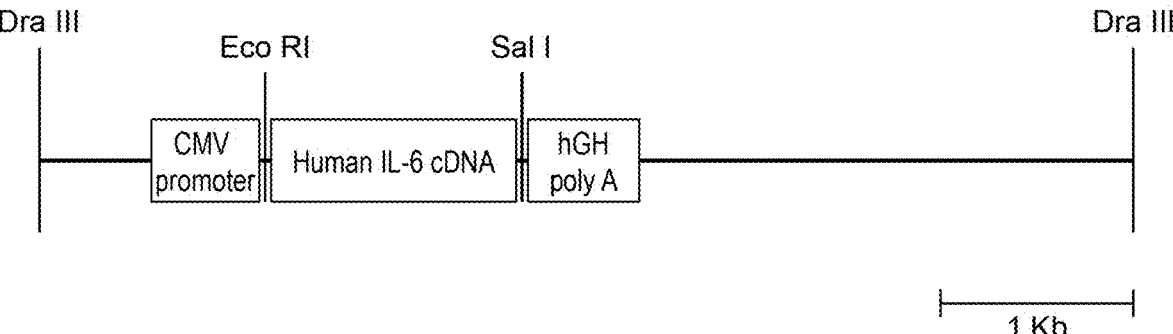
FIG. 1 shows a structure of a human interleukin 6 gene expression unit.

Hereafter, the present invention is described in detail.

The present invention relates to a non-human vertebrate comprising human liver cells transplanted therein and a method for producing the same.

The transgenic vertebrate comprising human liver cells transplanted therein of the present invention is a vertebrate to which human interleukin 6 (hereafter, referred to as "human IL-6") has been administered or an animal in which human liver cells are engrafted in the liver as a result of transplantation of human liver cells to a vertebrate that carries the human IL-6 gene in an expressible manner in vivo.

Examples of vertebrates include, but are not limited to, mice, rats, rabbits, dogs, cats, miniature pigs, pigs, and monkeys. Examples of monkeys include marmosets.

Animals into which human liver cells are to be transplanted in the present invention are animals that would not eliminate human IL-6 and human liver cells by the immune system; that is, animals that show inactivated immune responses to humans. Examples of such animals include animals that show inactivated immune responses to humans because of lowered or impaired immune functions. For example, immunodeficient animals or immune tolerant animals can be employed.

Immunodeficient animals have lowered or impaired immune functions, and such animals lack some or all of T cells, B cells, NK cells, dendritic cells, and macrophages. Immunodeficient animals can be prepared by applying x-rays to the entire bodies thereof, or animals having immune functions that have been genetically impaired can be used. The term "immune tolerant animals" refers to animals in which specific immune responses to particular antigens have been impaired or suppressed. In the present invention, such animals have established immune tolerance to human IL-6 and human liver cells. Human IL-6 and human liver cells are administered to animals to have the animals to acquire immune tolerance to human IL-6 and human liver cells. In order to have animals to acquire immune tolerance, human IL-6 and human liver cells may be administered to animals by means of hypodermic injection or via an oral route.

In the present invention, immunodeficient animals and immune tolerant animals are referred to as "animals that have impaired or lowered immune responses to humans."

While immunodeficient animal species are not limited, immunodeficient mice, immunodeficient rats, immunodeficient pigs, and the like can be preferably used.

Examples of immunodeficient mice include nude mice, NOD/SCID mice, Rag2 knockout mice, mice prepared by administering the asialo GM1 antibody or TMβ1 to SCID mice, and x-ray-irradiated mice. Knockout animals prepared by mating NOD/SCID mice or Rag2 knockout mice with IL-2Rγ knockout mice (hereafter, referred to as "dKO (double knockout) animals") can also be used. For example, dKO mice (Rag2 KO, IL-2R$^{null}$) can be used. In the present invention, dKO mice with the Balb/c background are referred to as "Balb/c dKO mice," and mice with the NOD background are referred to as "NOD dKO mice." The genetic backgrounds of mice are not limited to those described above, C57BL/6, C3H, DBA2, and IQI lineages, lineages with the SCID mutation and IL-2Rγ knockout or Rag2 knockout and IL-2Rγ knockout mutation, and impairment of the Jak3 proteins that is in charge of signal transmission downstream of the common γ chain of the IL-2 receptor are of the same phenotype with IL2Rγ$^{null}$. Accordingly, knockout mice prepared by mating Rag2 knockout mice with Jak3 knockout mice, knockout mice prepared by mating SCID mutation mice with Jak3 knockout mice, or inbred, outbred, or crossbred (F1 hybrid) mice thereof may be used.

In order to eliminate the influence of immune cells such as NK cells observed in such mice, transgenic immunodeficient mice in which the IL-2 receptor γ chain is impaired upon introduction of a mutation into the IL-2 receptor γ chain gene and SCID mutations of the genes associated with reconstruction of antigen receptor genes of T cells and B cells are present in both allele loci may also be used in the present invention, in addition to the SCID mice comprising the asialo GM1 antibody administered thereto as described above. Examples of such mice include NOG mice (NOD/SCID/γc$^{null}$ (NOD/Shi-scid, IL-2RγKO mice)), NSG mice (NOD/Scid/IL2Rγ$^{null}$ (NOD.Cg-Prkdc$^{scid}$IL2rg$^{tm1Wjl}$/SzJ)), and NCG mice (NOD-Prkdc$^{em26Cd52}$IL2rg$^{em26Cd22}$/NjuCrl) that are derived from the NOD/SCID mice in which the IL-2 receptor common γ chain is knocked out. Also, transgenic immunodeficient NOJ mice (NOD/Scid/Jak3nun (NOD.Cg-Prkdc$^{scid}$Jal3$^{tm1card}$) in which a mutation has been introduced into the Jak3 gene to impair Jak3 and SCID mutations of the genes associated with reconstruction of antigen receptor genes of T cells and B cells are present in both allele loci can be used. Hereafter, animals that have lost functions of the Prkdc gene and gene products thereof due to scid mutation or the like and that have lost regular functions of the IL2Ry gene products due to impairment or mutation of the IL2Ry gene or impaired functions of the gene located downstream of the signal transmission and gene products thereof are referred to as "NOG Mice®" and such animals can be used as hosts. Since lymphocytes are not observed in such mice, NOG mice do not exert NK activity, and NOG mice have impaired dendritic cell functions. The method for producing NOG mice is described in WO 2002/043477. The method for producing NSG mice is described in Ishikawa F. et al., Blood 106: 1565-1573, 2005, the method for producing NCG mice is described in Zhou J. et al. Int. J. Biochem. Cell Biol., 46: 49-55, 2014, and the method for producing NOJ mice is described in Okada S. et al., Int. J. Hematol., 88: 476-482, 2008.

It is preferable that the non-human vertebrates that have impaired or lowered immune responses, such as the immunodeficient animals, used in the method of the present invention be induced to have liver injury by various methods of liver injury induction. The liver cells of the non-human vertebrates induced to have liver injury are replaced with human liver cells transplanted therein, and the transplanted human liver cells are engrafted in the liver of the non-human vertebrates.

Examples of various methods of liver injury induction include the following methods:

(i) a method of liver injury induction in the liver of a non-human vertebrate that has impaired or lowered immune reactions against humans and carries the thymidine kinase gene in an expressible manner by administering human liver cells and suicide substrates to the non-human vertebrate;

(ii) a method of liver injury induction in the liver of a non-human vertebrate that has impaired or lowered immune reactions against humans by allowing the urokinase-type plasminogen activator gene to be carried in an expressible manner therein;

(iii) a method of liver injury induction by impairing the fumarylacetoacetate hydrolase (Fah) gene of the non-human vertebrate that has impaired or lowered immune reactions against humans; and (iv) a method of liver injury induction by administering any of the compounds (a) to (e) below:
(a) carbon tetrachloride;
(b) acetaminophen;
(c) d-galactosamine;
(d) thioacetamide; and
(e) anti-Fas antibody.

Hereafter, the methods are described in detail.

(i) A method of liver injury induction in the liver of a non-human vertebrate that has impaired or lowered immune reactions against humans and carries the thymidine kinase gene in an expressible manner by administering human liver cells and suicide substrates to the non-human vertebrate In the method described above, the thymidine kinase gene is carried in an expressible manner in the liver of a non-human vertebrate.

Hereafter, a case in which a non-human vertebrate is a mouse is described, and the example of a mouse can be applied to other non-human vertebrates. The immunodeficient mouse used in the method of the present invention comprises the thymidine kinase gene carried in an expressible manner in the mouse liver. When a mouse "comprises the thymidine kinase gene carried in an expressible manner in the mouse liver," the thymidine kinase gene is included in the mouse liver cells and expressed therein. Specifically, a foreign thymidine kinase gene is introduced to be expressed specifically in the mouse liver. The origin of the thymidine kinase gene is not particularly limited, the thymidine kinase gene may be derived from a human, a mammal, a procaryotic cell, or a virus, and it is preferably human herpes simplex virus type 1-thymidine kinase (HSV-tk). A mutant of any of such thymidine kinase genes may be used. An example of a mutant is HSV-tk mutant clone #30. HSV-tk mutant clone #30 is described in PNAS 1996, Vol. 93, pp. 3525-3529. HSV-tk mutant clone #30 is referred to as "TK mutant 30." SEQ ID NO: 1 shows the nucleotide sequence of wild-type HSV-tk, SEQ ID NO: 2 shows the amino acid sequence of wild-type HSV-tk, SEQ ID NO: 3 shows the nucleotide sequence of the TK mutant 30, and SEQ ID NO: 4 shows the amino acid sequence of the TK mutant 30. In the present invention, the TK mutant 30 and other mutants are within the scope of HSV-tk. A suicide substrate that exerts toxicity when it is metabolized by thymidine kinase exerts cytotoxicity selectively on cells having thymidine kinase activity as a result of introduction of the thymidine kinase transgene. Thus, such suicide substrate is used as a selective therapeutic agent that exerts cytotoxicity selectively on the target cell. A guanosine analog can be used as such a suicide substrate. Examples of preferable guanosine analogs include ganciclovir (GCV), valganciclovir (valGCV), and aciclovir that are commonly used as antivirus agents.

When a mouse "comprises the thymidine kinase gene carried in an expressible manner in the mouse liver," the thymidine kinase gene is included in the mouse liver cells and expressed therein.

In order to allow the thymidine kinase gene of the present invention to be carried in an expressible manner in the mouse liver, a regulatory gene that functions in the liver can be adequately used. A regulatory gene of a gene encoding a protein that functions in the liver cell is used as the regulatory gene described above. The term "regulatory gene" used herein refers to a sequence on DNA that is involved in enhanced/lowered gene transcription efficiency, and examples thereof include, but are not limited to, a promoter, an enhancer, an upstream activating sequence, a silencer, an upstream repressing sequence, and an attenuator. An organism species from which the regulatory gene is derived is not limited to a particular organism species. A mouse-derived regulatory gene can be used to realize more adequate gene expression in the mouse liver.

The promoter is not particularly limited, provided that it enables the thymidine kinase gene to be expressed in the liver. Examples of promoters include an albumin promoter, a transthyretin promoter, a thyroxine binding globulin promoter, an organic anion transporter LST-1 promoter, an α-fetoprotein promoter, and an α-tocopherol transport protein (α-TTP) gene promoter.

The expression mechanism of a gene that is expressed in a liver-specific manner has been well studied (gene promoter analysis). Specifically, it is known that an ubiquitous transcription regulatory factor binding site, sites to which liver-specific transcription factors that are abundantly present in the liver bind, and an upstream activating sequence that responds to extracellular stimuli such as hormones are present in a relatively narrow region in the 5' upstream region of the transcription initiating point of a gene expressed in a liver-specific manner. Preferable examples of such transcription factors include HNF-1, HNF-3, HNF-4, HNF-6, C/EBP, and DBP. In the present invention, the thymidine kinase gene is ligated to the upstream activating sequence that functions in the mouse liver to have the thymidine kinase gene to be carried in an expressible manner in the mouse liver.

For example, a certain region of the albumin promoter, the transthyretin promoter, the thyroxine binding globulin promoter, the organic anion transporter LST-1 promoter, the α-fetoprotein promoter, or the α-tocopherol transport protein (α-TTP) gene promoter region is used for the ligation described above. Thus, an upstream activating sequence to which a ubiquitous liver-specific transcription factor binds can be used. In another embodiment, a liver-specific upstream activating sequence having the identified sequence can be incorporated as a foreign gene via genetic recombination.

An enhancer that enhances a transcription level from the promoter is known to be present in a region downstream of the transcription initiation point in addition to the upstream activating sequence. In a transgenic mouse comprising a 14-kb human angiotensinogen gene (full-length) including a 1.3-kb 5'-upstream region and a 3'-downstream region, for example, a high level expression of such gene is observed in the liver. In a human liver cancer-derived HepG2 cell, in addition, the presence of the enhancer is observed in a 3.8-kb DNA fragment located downstream of the gene transcription initiation point. In the present invention, such enhancer can be preferably used to express the thymidine kinase gene in a liver-specific manner.

In the present invention, in addition, a 3'-untranslated sequence including a poly A addition signal can be used to express the thymidine kinase gene in a liver-specific manner.

In the present invention, the thymidine kinase gene is ligated to the upstream activating sequence that functions in the mouse liver, so that the thymidine kinase gene is carried in an expressible manner in the mouse liver. A 3'-untranslated sequence including an enhancer, a poly A addition signal, and the like can further be ligated. The genes thus ligated are inserted into a vector comprising a marker gene, such as a drug resistant gene, so as to construct an integration vector that prepare a gene expression unit to allow the thymidine kinase gene to be carried in an expressible manner in the host liver.

A transgenic mouse into which the gene expression unit prepared by the integration vector has been introduced can be prepared. For example, a transgenic mouse can be prepared in accordance with a conventional technique (Proc. Natl. Acad. Sci., U.S.A., 1980, 77, 7380-4).

Specifically, a gene expression unit prepared to allow the target thymidine kinase gene to be carried in an expressible manner in the host liver is introduced into the mouse totipotent cell. Examples of preferable totipotent cells into which the gene of interest is to be introduced include a fertilized egg, an early embryo, and cultured cells such as pluripotent ES cells and iPS cells. For example, a female mouse to which an ovulation inducing agent has been administered is subjected to mating with a normal male mouse. Thus, a fertilized egg into which the gene expression unit can be introduced can be preferably collected. In general, a gene expression unit is introduced into the mouse fertilized egg via microinjection into the male pronucleus. Following fertilized egg cell culture in vitro, cells into which the gene expression unit has been successfully introduced are screened for. The screened cells are transplanted into the ovarian duct of the surrogate mother, and transgenic chimeric mice are then generated. In general, a female mouse that is made pseudopregnant via mating with a male mouse with a seminal duct being cut therefrom is used as a surrogate mother.

Mice into which transgenes have been integrated into somatic cells and germ cells are selected from among the resulting plurality of mice. Thus, target transgenic mice can be prepared.

An example of mice comprising the thymidine kinase gene carried in an expressible manner in the liver is transgenic mice resulting from introduction of a target thymidine kinase gene designed to be carried in an expressible manner in the host liver into a fertilized egg of the immunodeficient mouse. In addition, it is possible to use immunodeficient mice selected as mice that retain traits of immunodeficient mice and carry the target thymidine kinase gene in an expressible manner in the host liver from among offspring mice resulting from mating between the immunodeficient mice described above and transgenic mice resulting from introduction of the gene of interest into the fertilized egg of inbred mice of the immunodeficient mice that have not lost the immune functions. In the present invention, mice selected as those that retain traits of NOG mice and carry the target thymidine kinase gene in an expressible manner in the host liver are referred to as "TK-NOG mice." The method for preparing the TK-NOG mice is described in JP Patent No. 507,836. Examples of thymidine kinase genes carried by the TK-NOG mice include human herpes simplex virus type 1-thymidine kinase (HSV-tk) and mutants thereof. An example of a mutant is the HSV-tk mutant clone #30 (TK mutant 30) described above. Mice that carry TK mutant 30 are referred to as "TKmut30-NOG mice." In the present invention, TKmut30-NOG mice are within the scope of TK-NOG mice. TKmut30-NOG mice can be prepared in the same manner as with the method for preparing TK-NOG mice. Specifically, the Alb promoter of the expression unit used for preparation of TK-NOG mice is replaced with the transthyretin promoter, and cDNA of the HSV-tk gene (from the initiation codon to the termination codon) is replaced with cDNA of the HSV-tk mutant 30 gene (from the initiation codon to the termination codon). Thus, the TKmut30-NOG mice can be prepared. Examples of genotypes of TK-NOG mice include NOD.Cg-Prkdc$^{scid}$Il2rg$^{tm1Sug}$Tg (Alb-UL23)7-2/ShiJic mice (TK-NOG), NOD.Cg-Prkd$^{scid}$Il2rg$^{tm1Sug}$Tg (Ttr-UL23 mutant 30)4-9/ShiJic mice (TKmut30-4-9-NOG), NOD.Cg-Prkdc$^{scid}$Il2rg$^{tm1Sug}$ Tg (Ttr-UL23 mutant 30)5-2/ShiJic mice (TKmut30-5-2-NOG), and NOD.Cg-Prkdc$^{scid}$Il2rg$^{tm1Sug}$ Tg (Ttr-UL23 mutant 30)10-15/ShiJic mice (TKmut30-10-15-NOG).

In addition, it is possible to use immunodeficient mice selected as mice that retain traits of immunodeficient mice and carry the target thymidine kinase gene in an expressible manner in the host liver from among offspring mice resulting from mating between the immunodeficient mice described above and transgenic mice resulting from introduction of the gene of interest into the fertilized egg of inbred mice of the immunodeficient mice that have partially impaired immune functions. More specifically, preferable examples include mice that retain traits of NOG mice and carry the target thymidine kinase gene in an expressible manner in the host liver selected from among offspring mice generated as a result of mating between NOG mice and NOD/SCID transgenic mice resulting from introduction of the gene of interest into the fertilized egg of NOD/SCID mice, TK-Balb/cA dKO mice (HSV-Tk (+), SCID wild, RAG-2 KO, IL-2R$^{null}$) resulting from mating between TK-NOG mice and Balb/cA dKO mice (RAG-2KO, IL-2R$^{null}$), followed by mating between the resultant and Balb/cA dKO mice, TK-NOD dKO mice (HSV-Tk (+), SCID wild, RAG-2 KO, IL-2R$^{null}$) resulting from mating between TK-NOG mice and NOD dKO mice (RAG-2 KO, IL-2R$^{null}$) followed by mating between the resultant and NOD dKO mice, TK-IQI/NOG F1 mice (HSV-Tk (+), SCID, IL-2R$^{null}$) resulting from mating between TK-NOG mice and IQI/SCID, IL-2R$^{null}$ mice, and TK-IQI SCID, IL-2R$^{null}$ mice resulting from repeated mating with IQI/SCID, IL-2R$^{null}$ mice.

When the guanosine analog is administered to a mouse comprising the thymidine kinase gene of the present invention carried in an expressible manner in the liver, the guanosine analog is metabolized into a toxic substance in the mouse liver cells, and the mouse would develop liver injury as a consequence. Ganciclovir, which is a preferable example of the guanosine analog, is metabolized into ganciclovir triphosphate in the mouse liver cells, and it induces liver injury in the mouse. A method for administration of a guanosine analog to the mouse can be freely selected. For example, intravenous administration, intramuscular administration, subcutaneous administration, intradermic administration, intraperitoneal administration, or application to the skin can be adequately adopted. In addition to the administration to the mouse via such common route, the guanosine analog can be incorporated into feeds or water and administered to the mouse. While the amount of the guanosine analog to be administered is not limited, it is 0.1 to 10 mg/kg of body weight, and it is preferably 0.5 to 1.5 mg/kg of body weight. The guanosine analog may be added to water at a concentration of 0.05 to 0.5 mg/ml, and the mouse may be allowed to freely drink water for 1 day to 1 week.

In addition, a mouse comprising the thymidine kinase gene of the present invention carried in an expressible manner in the liver can be induced to have liver injury by, in addition to ganciclovir administration described above, treatment with known liver injury inducing agents such as carbon tetrachloride, D-galactosamine, pyrrolidine alkaloid, or 2-acetylaminofluorene, or surgical treatment such as surgical hepatic resection. According to another embodiment, a mouse can be induced to have liver injury via administration of the anti-mouse Fas antibody to the mouse. The anti-mouse Fas antibody does not bind to the Fas antigen that is expressed in a human liver cell but it binds to the Fas antigen that is expressed in a mouse liver cell. Thus, it induces apoptosis specifically in the mouse liver cell.

(ii) A method for liver injury induction in the liver of a non-human vertebrate that has impaired or lowered immune reactions against humans by allowing the non-human vertebrate to carry the urokinase-type plasminogen activator gene in an expressible manner in the liver A mouse that has NOG mutation; i.e., the urokinase-type plasminogen activator gene is carried in an expressible manner in the liver instead of the thymidine kinase gene, can also be used. Specifically, a transgenic mouse resulting from introduction of a gene expression unit prepared to have the urokinase-type plasminogen activator gene to be carried in an expressible manner in the host liver into a totipotent cell of the mouse having NOG mutation can be used. As the urokinase-type plasminogen activator gene, a polynucleotide encoding a mouse urokinase-type plasminogen activator can be used. Such mouse is referred to as the uPA-NOG mouse, and it can be prepared in accordance with Suemizu H. et al., Biochem. Biophys. Res. Commun., 377, 248, 2008.

In addition, a mouse having NOG mutation; i.e., both the thymidine kinase gene and the urokinase-type plasminogen activator gene are carried in an expressible manner in the liver, can also be used. The time at which liver injury is induced by the action of the thymidine kinase and the time at which liver injury is induced by the action of the urokinase-type plasminogen activator are adequately selected, so that engraftment of the human liver cells administered can be optimized.

Such mouse can be obtained by adequate crossbreeding between, for example, a mouse comprising the thymidine kinase gene carried in an expressible manner in the liver and a mouse having NOG mutation, such that the urokinase-type plasminogen activator gene is carried in an expressible manner in the liver, and selecting an offspring mouse having desirable traits; i.e., both the thymidine kinase gene and the urokinase-type plasminogen activator gene are carried in an expressible manner in the liver, and NOG mutation. Also, a mouse of interest can be prepared by, for example, introducing a gene expression unit prepared to have the urokinase-type plasminogen activator gene to be carried in an expressible manner in the host liver into a totipotent cell of a mouse comprising the thymidine kinase gene carried in an expressible manner in the host liver.

(iii) A method for liver injury induction by impairing the fumarylacetoacetate hydrolase (Fah) gene of a non-human vertebrate that has impaired or lowered immune reactions against humans A method for liver injury induction by impairing the Fah gene is described in Azuma H. et al., Nat. Biotechnol., 25, 8, 2007. Also, Faysal Elgilano et al., Am. J. Pathol., 187, 1, 2017 describes that an animal lacking the Fah gene was prepared using a pig via CRISPR/Cas9 genome editing.

For example, a chimeric pig with a human liver can be easily prepared with the use of an immunosuppressor or via impairment of the gene associated with the immune system via CRISPR/Cas9 genome editing.

(iv) A method for liver injury induction by administering any of the compounds (a) to (e) below:
   (a) carbon tetrachloride;
   (b) acetaminophen;
   (c) d-galactosamine;
   (d) thioacetamide; or
   (e) anti-Fas antibody.

Such compounds are known as chemical substances that damage the liver.

Animals with lowered immunity against human liver cells (genetically immunodeficient animals, animals with immune tolerance as a result of sensitization in the fetal period to the neonatal period, or animals with immunity lowered with the use of immunosuppressors) can be induced to have liver injury via administration of chemical substances as described above thereto, and human liver cells can be transplanted and engrafted therein.

Any of the methods (i) to (iv) may be performed alone, or 2, 3, or 4 of the methods (i) to (iv) above may be performed in combination.

A vertebrate used to prepare the vertebrate of the present invention comprising human liver cells transplanted therein may be prepared by allowing human IL-6 to be present in the body of the immunodeficient animal.

Examples of methods of having human IL-6 to be present in vivo include the following:
   1. a method of introducing the human IL-6 gene into the immunodeficient animal in an expressible manner and expressing the same therein; and
   2. a method of administering human IL-6 to the immunodeficient animal.

Specific examples of the method 1 include:
   (1) a method of subjecting an immunodeficient animal to mating with a human IL-6 transgenic animal resulting from introduction of the human TL-6 gene into the immunodeficient animal in an expressible manner;
   (2) a method of administering cultured cells in which the human IL-6 gene is expressed to the immunodeficient animal to have the immunodeficient animal to carry the same; and
   (3) a method of inoculating the immunodeficient animal with the human IL-6 gene expression vector.

The method of subjecting an immunodeficient animal to mating with a human IL-6 transgenic animal resulting from introduction of the human IL-6 gene into the immunodeficient animal in an expressible manner (1) can be performed in accordance with, for example, the process described below.

A human IL-6 gene expression unit may be introduced into the human IL-6 transgenic animal into which the human IL-6 gene has been introduced in an expressible manner. The human IL-6 gene expression unit comprises a promoter and an enhancer, and it may further comprise an element, such as a poly A additional sequence. An example of the human IL-6 expression unit is shown in FIG. 1.

(i) a Step of Injecting a DNA Fragment Comprising Human IL-6 cDNA into a Fertilized Egg of an Immunodeficient Animal In this step, a vector into which a DNA fragment comprising human IL-6 cDNA has been introduced may be used. A DNA fragment may be injected via, for example, microinjection or electroporation.

(ii) a Step of Culturing the Fertilized Egg Comprising a DNA Fragment Injected Thereinto Obtained in (i) to Obtain a Newborn Animal An animal obtained in this step is referred to as "a human IL-6 transgenic founder animal." A newborn animal can be obtained from a fertilized egg by, for example, culturing a fertilized egg comprising a DNA fragment injected thereinto in vitro for 18 to 24 hours at 30° C. to 40° C., transplanting the cultured fertilized egg into the uterus of the surrogate mother, and allowing the transplanted fertilized egg to be engrafted therein.

(iii) a Step of Subjecting the Founder Animal Obtained in (ii) to Mating with an Immunodeficient Animal When the TK gene is to be introduced, an animal comprising the TK gene introduced thereinto may be subjected to mating.

The animal thus obtained is an immunodeficient animal that expresses human IL-6 in vivo.

When a TK-NOG mouse is used as an immunodeficient animal, for example, it is prepared in the manner described below.
   (i) A DNA fragment comprising human IL-6 cDNA is microinjected into a fertilized egg obtained by mating a female NOD mouse and a male NOG mouse to obtain a human IL-6 transgenic founder mouse.

(ii) The human IL-6 transgenic founder mouse is subjected to mating with a NOG mouse to obtain a scid-IL2Rg$^{null}$ mutant mouse. This mouse is referred to as "NOG-IL-6."

(iii) The NOG-IL-6 mouse is subjected to mating with the TK-NOG mouse. Among the resulting mice, mice that carry both the human IL-6 transgene and the HSVtk transgene are referred to as "TK-NOG-IL-6 mice." Such mice are represented by gene symbols: for example NOD.Cg-Prkdc$^{scid}$Il2rg$^{tm1Sug}$ Tg ((Alb-UL23) 7-2, CMV-IL-6)/ShiJic (TK-NOG-IL-6), NOD.Cg-Prkdc$^{scid}$Il2rg$^{tm1Sug}$Tg (Ttr-UL23 mutant 30)4-9, and CMV-IL-6/ShiJic mice (TKmut30-4-9-NOG-IL-6); NOD.Cg-Prkdc$^{scid}$Il2rg$^{tm1Sug}$ Tg (Ttr-UL23 mutant 30)5-2, CMV-IL-6/ShiJic mice (TKmut30-5-2-NOG-IL6); and NOD.Cg-Prkdc$^{scid}$Il2rg$^{tm1Sug}$ Tg (Ttr-UL23 mutant 30)10-15, and CMV-IL-6/ShiJic mice (TKmut30-10-15-NOG-IL6).

By transplanting human liver cells to the non-human vertebrates comprising human IL-6 in vivo thus obtained, non-human vertebrates comprising human liver cells transplanted therein can be prepared. When non-human vertebrates involve genetic modification, they are referred to as "transgenic non-human vertebrates."

Examples of methods for transplanting human liver cells into non-human vertebrates that can be adequately employed include a method of transplantation through the spleen to the liver of non-human vertebrates and a method of direct transplantation through a portal vein. Alternatively, human liver cells may be transplanted intraperitoneally or intravenously. The number of human liver cells to be transplanted in a single instance can be adequately selected from 1 to 2,000,000 (2×10$^6$) cells.

Common liver cells that are maintained (including culture, subculture, and storage) in the presence of serum (e.g., fetal bovine serum), primary liver cells, and established liver cells can be preferably used. Human liver cells subjected to transplantation may be of any origins, provided that such cells are present in the human liver including hepatic parenchymal cells. When normal liver cells are used, liver cells obtained from the subject's liver tissue can be used. Liver tissue can be sampled by, for example, a conventional biopsy, in addition to surgical resection. Liver biopsy is a method of directly introducing a thin long needle through the skin into the liver to sample liver tissue. In general, a needle is punctured through the intercostal space in the lower right chest. Before surgery, safety of the puncture site is confirmed using an ultrasound detector, and the puncture site is sterilized. In addition, an area from the skin to the liver surface is to be anesthetized, and a needle is introduced through a small incision formed on the skin of the puncture site. In addition, commercially available frozen human liver cells can be used.

When primary liver cells are used, liver cells are adequately isolated from the sampled liver or liver tissue by fractionating a cell suspension comprising liver cells dispersed in, for example, a Hanks' balanced salt solution ice-cooled via a conventional technique such as perfusion or permeation via centrifugation or other means. The obtained liver cells are adequately cultured in a medium such as Williams' E supplemented with bovine serum in the presence of 5% CO$_2$ at 37° C. for 24 hours. In addition, the cells cultured in the medium that is exchanged with a medium such as ASF104 (Ajinomoto Co., Inc.) every 3 days for approximately 1 week can be used. The medium can be supplemented with cell growth factors such as HGF and EGF, and the culture matrix, three-dimensional culture matrix, and the like can be adequately modified.

When established liver cells are used, liver cell types are not particularly limited. Examples thereof include SSP-25, RBE, HepG2, TGBC50TKB, HuH-6, HuH-7, ETK-1, Het-1A, PLC/PRF/5, Hep3B, SK-HEP-1, C3A, THLE-2, THLE-3, HepG2/2.2.1, SNU-398, SNU-449, SNU-182, SNU-475, SNU-387, SNU-423, FL62891, and DMS153. These cells can be obtained from American Type Culture Collection (ATCC) or other institutions. For example, Hep3B and HepG2 are registered under ATCC HB-8064 and ATCC HB-8065, respectively, and HuH-7 is registered under JCRB0403 at the JCRB Cell Bank, National Institutes of Biomedical Innovation, Health, and Nutrition.

When a non-human vertebrate that has impaired or lowered immune reactions against humans is used, the animal may be induced to have liver injury via a method of liver injury induction. When human liver cells are administered to an animal, the human liver cells transplanted in the animal are engrafted in the liver thereof instead of liver cells of the animal that was induced to have liver injury. While animal liver cells die, human liver cells engrafted in the animal liver grow. Thus, a chimeric animal comprising a given number or more human liver cells can be prepared. In such chimeric animal, 50% or more, preferably 70% or more, more preferably 75% or more, further preferably 80% or more, still further preferably 90% or more, and particularly preferably 95% or more, 96% or more, or 97% or more of the animal liver cells is replaced with human liver cells. This replacement rate is also referred to as a chimeric rate.

When an immunodeficient animal comprising the TK gene introduced thereinto or an animal that has acquired immune tolerance against IL-6 is used, a guanosine analog or the like may be administered. A guanosine analog and human liver cells may be administered simultaneously or separately from each other to an animal. For example, a guanosine analog may be administered intraperitoneally to an animal. Alternatively, a guanosine analog may be mixed with water, the resultant may be fed to an animal, and human liver cells may then be transplanted to the animal through the spleen or the vein.

Replacement of animal liver cells with human liver cells is referred to as repopulation of human liver cells or the liver, and an animal prepared by replacement of animal liver cells with human liver cells to repopulate the liver is referred to as a chimeric animal with repopulated human liver cells or a chimeric animal with the repopulated human liver. When an animal is a mouse, it is referred to as a chimeric mouse with repopulated human liver cells or a chimeric mouse with the repopulated human liver. The liver in which liver cells have been replaced with human liver cells is referred to as the humanized liver.

The present invention encompasses the human liver tissue repopulated in an animal such as a mouse. The liver tissue has a three-dimensional structure or functions of the human liver, and 75% or more, preferably 80% or more, more preferably 90% or more, and particularly preferably 95% or more, 96% or more, or 97% or more of the liver cells of a non-human vertebrate is replaced with human liver cells to repopulate the liver. Also, the repopulated liver has the hepatobiliary tract system of the human liver constructed therein, it has the structure of the functional lobule of the human liver, and the hepatic excretory function of foreign bodies normally works.

For example, a case in the presence of human IL-6 is compared with a case in the absence of human IL-6. When a TK-NOG-IL-6 mouse is used, specifically, the human liver cell growth rate is faster and the chimeric rate of human liver cells (the engraftment rate) is higher, compared with the case in which a TK-NOG mouse is used in the absence of human IL-6. For example, the human liver cell count of a mouse is correlated with the human albumin concentration in the blood of the mouse. When the human albumin concentration in the blood of the mouse to which human liver cells had been transplanted is used as an indicator to compare the human liver cell growth ability, accordingly, the growth rate in the TK-NOG-IL-6 mouse is 2 times higher than that in the TK-NOG mouse 2 weeks after transplantation, and such growth rate is at least 1.2 times, preferably at least 1.3 times, and more preferably at least 1.4 times higher than the growth rate in the TK-NOG mouse 4 weeks after transplantation. The TK-NOG-IL-6 mice exhibiting a chimeric rate of higher than 70% (the replacement index of 70%) relative to all the mice to which the liver cells had been transplanted is 80% or higher 4 weeks after transplantation and thereafter. In contrast, TK-NOG mice exhibit a chimeric rate of 10% or lower or 50% or lower. When the percentage of mice exhibiting a chimeric rate of 70% or higher is used as an index, a chimeric rate (engraftment rate) of human liver cells in TK-NOG-IL-6 mice is at least 1.3 times higher, and preferably at least 1.4 times higher than that of TK-NOG mice.

When human liver cells are transplanted into a transgenic non-human vertebrate in the presence of human IL-6 in vivo, the human liver cell doubling time in the non-human vertebrate is shorter than that in a transgenic non-human vertebrate into which human liver cells have been transplanted in the absence of IL-6.

When human liver cells are transplanted into a TK-NOG-IL-6 mouse, for example, the human liver cell doubling time therein is shorter than that in a TK-NOG mouse into which human liver cells have been transplanted in the absence of IL-6.

The human liver cell doubling time when a chimeric mouse with a human liver is used can be determined in the manner described below.

At the outset, the liver of a chimeric mouse with a human liver is subjected to collagenase perfusion to collect all the liver cells. The number of the collected cells is determined via trypan blue staining. A HLA-positive cell rate (human cell rate) is determined via flow cytometric analysis. The number of the collected cells is multiplied by the HLA positive rate to determine the number of the collected human cells. The doubling time and the like can be determined in accordance with the equations shown below.

$$\text{Time after cell transplantation(the number of days)} = \text{the date of isolation and collection of liver cells}-\text{the date of liver cell transplantation}$$

$$\text{Growth rate(doubling)}=(\text{the number of collected cells}\times\text{the HLA positive rate})/\text{the number of transplanted cells}$$

$$\text{Frequency of cell division(the number of times)}=\text{LOG(multiplication factor:2)}$$

$$\text{Doubling time(the number of days)}=\text{the time after cell transplantation/the frequency of cell division}$$

When human liver cells are transplanted into TK-NOG-IL-6 mice, the human liver cell doubling time in the mouse body is within 2.4 days (56.9 hours) at the shortest, and it is preferably within 3 days (72.0 hours). When human liver cells are transplanted into TK-NOG-IL-6 mice, the human liver cell doubling time in the mouse body is at least 1.2 times, preferably at least 1.3 times, more preferably at least 1.4 times, and particularly preferably at least 1.5 times shorter than that in the body of TK-NOG mice into which human liver cells have been transplanted. Specifically, the growth rate upon transplantation of human liver cells to TK-NOG-IL-6 mice is at least 1.2 times, preferably at least 1.3 times, more preferably at least 1.4 times, and particularly preferably at least 1.5 times faster than that in the body of TK-NOG mice into which human liver cells have been transplanted.

Histology and immunohistochemistry demonstrate that the foci disappear 4 weeks after transplantation and most of liver cells is replaced with human liver cells in TK-NOG-IL-6 mice. While the foci in the liver observed in TK-NOG mice are in the state of the grown cultured cells, the foci in the liver observed in TK-NOG-IL-6 and Tkmut30-NOG-IL-6 mice are apparently different from the grown cultured cells, a sinusoid-like structure is observed, the structure of the liver lobule is similar to the lobular structure of a human, and a portal triad composed of the interlobular artery, the interlobular vein, and the interlobular bile duct is satisfactorily conserved. High chimeric efficiency according to the present invention; i.e., earlier mouse liver cell death, would exert unexpected effects, such that human liver tissue would be histologically repopulated. According to the present invention, specifically, the human liver would be more efficiently repopulated in terms of albumin production according to a physiological aspect.

To chimeric animals comprising human liver cells, human liver cells are administered, and test substances are then administered thereto, for example, approximately 60 days thereafter. An example of a test substance is a drug candidate substance. A drug candidate substance is a substance that is in the process of drug development, and a preferable example is a substance that necessitates prediction of drug interactions in humans. Such substance can be a main ingredient exerting drug efficacy or a compound comprising such main ingredient. The amount of a drug candidate substance to be administered varies depending on, for example, a target disease, a composition, or a route of administration, and it can be adequately selected from the range of approximately 0.1 mg/kg to 2,000 mg/kg per body weight. A route of administration can be adequately selected from among oral, percutaneous, subcutaneous, intravenous, intraperitoneal, and other routes in accordance with a type of the drug candidate substance or a suitable dosage form.

An extent of metabolism of a test substance, such as a drug candidate substance, and a metabolite in the liver of a chimeric animal can be adequately measured and identified by measuring the drug candidate substance concentration in the mouse plasma via a conventional technique in the art, such as chromatography. Measurement can be performed at a single time point or a plurality of time points with the elapse of time that is or are adequately selected from a duration of approximately 30 minutes to 24 hours after administration of the candidate substance.

Based on the concentration of the drug candidate substance in the plasma and the concentration of the substance metabolized by a drug-metabolizing enzyme in the liver, whether or not the drug candidate substance of interest is likely or less likely to be metabolized by a subject that lacks, for example, CYP2D6, CYP2C9, or CYP2C19 can be determined.

Examples of drug-metabolizing enzymes of humans include CYP1A1, CYP1A2, CYP1B1, CYP2A6, CYP2B6, CYP2C8, CYP2C9, CYP2C10, CYP2C18, CYP2C19, CYP2D6, CYP2E1, CYP3A3, CYP3A4, CYP3A5, CYP3A7, CYP4F1, CYP4A2, and CYP4A3 that belong to the CYP enzyme family. For example, an index compound metabolized by CYP1A2 is caffeine, that metabolized by CYP2C9 is tolbutamide, that metabolized by CYP2D6 is dextromethorphan, that metabolized by CYP2C19 is omeprazole, and that metabolized by CYP3A4 is erythromycin.

After the drug candidate substance is administered to the chimeric animal of the present invention, a mixture of index compounds is administered thereto, and the plasma concentration of each compound is measured with the elapse of time. Thus, whether or not the drug candidate substance of interest is a substance that accelerates or inhibit activity of each enzyme can be determined. When caffeine metabolism is accelerated and plasma concentration of caffeine is lowered upon administration of the drug candidate substance, for example, the drug candidate substance is determined to be a substance that specifically accelerates activity of CYP1A2.

Specifically, the way in which a drug administered to a human is metabolized in the human liver and a metabolite generated; i.e., drug dynamics, the metabolite, a metabolizing rate, and the like in the blood plasma, can be identified and evaluated with the use of the animal of the present invention. From the viewpoint of metabolism, an adequate drug to be administered to a human can be screened for, and an adequate dose of a drug to be administered to a human can be predicted. In addition, the animal of the present invention can be used for studies on growth and reproduction of the human liver.

A candidate drug can be administered by any of various desirable methods and/or an adequate method for drug delivery. For example, a candidate drug can be administered via injection (e.g., intravenous injection, intramuscular injection, subcutaneous injection, or direct injection into tissue to achieve desirable activity), orally, or any other preferable methods. In general, an in vivo screening method targets several types of animals exposed to candidate drugs at various doses and concentrations (from no drug administration to the maximal amount of a drug that can be sufficiently delivered to an animal), and it encompasses drug delivery methods at various dosage forms through various routes of administration. A drug can be administered by itself, or two or more types of drugs can be administered in combination when synergistic effects are exerted via administration of drugs in combinations of two or more.

Examples of candidate drugs to be screened for include synthetic molecules, natural molecules, and recombinant molecules (e.g., low-molecular-weight molecules, drugs, peptides, antibodies such as antigen-binding antibody fragments causing passive immunity, and other immunotherapeutic agents, such as endogenous factors contained in eucaryotic or procaryotic cells (e.g., polypeptides or plant extract)). An assay technique for screening for a drug exhibiting low toxicity on human cells is particularly important.

It is another object of the present invention to provide a mouse model that can be used for searching, detection, and identification of cells that can constitute the liver used for cell transplantation therapy in the future, such as liver stem cells. It is sufficient if liver stem cells are differentiated into liver cells in the future, and the number of generations necessary for differentiation into liver cells is not particularly limited. Specifically, the present invention provides a method of searching for and identifying the cells that can constitute the liver used for cell transplantation therapy in the future, such as human liver stem cells, from among the liver tissue engrafted in a mouse model upon transplantation of primary separated cells obtained from human liver tissue through the splenic portal vein therein. In addition, a cell population including cells that can constitute the liver used for cell transplantation therapy in the future, such as human liver stem cells, can be collected from among the engrafted liver tissue. The present invention also provides a method for collecting a cell population including cells that can constitute the liver used for cell transplantation therapy in the future, such as liver stem cells. A method that involves orthotropic graft instead of transplantation through the splenic portal vein can also be employed. Stem cells that are induced to differentiate into liver cells cultured under adequate conditions in a test tube can be used to attain the object of the present invention instead of primary separated cells. A method of inducing such stem cells to differentiate into liver cells is described in, for example, Gastroenterology, 2009, 136, 990-999. In order to search for and identify liver stem cells using the growth ability as the indicator from liver tissue, histological immunostaining can be performed using an antigen that recognizes a marker for liver cell detection and/or an antibody that recognizes cells capable of growing. A marker for liver cell detection can be adequately selected from among, for example, albumin, tyrosine aminotransferase, glucose-6-phosphatase, coagulation factor (CF) VII, asialoglycoprotein receptor, and cytokeratin 8/18. A cell growth marker can be adequately selected from among, for example, Ki-67 antigen, 5-bromo-2'-deoxyuridine incorporation ability, and PCNA. With the use of such markers, a cell population including human liver stem cells can be obtained, liver cells expressing such markers are adequately isolated with the use of FACS Calibur (Nippon Becton Dickinson Company, Ltd.), and isolated liver stem cells are adequately subjected to cell transplantation therapy and the like.

As described above, whether or not the human liver cells transplanted into a transgenic non-human vertebrate are engrafted and grown can be examined with the use of the human albumin concentration in the blood of a non-vertebrate as a human liver cell engraftment marker. In addition, substantially no cholinesterase activity is observed in the blood of a mouse etc. With the use of cholinesterase activity in the blood as a human liver cell engraftment marker, accordingly, whether or not the human liver cells transplanted into a transgenic non-human vertebrate are engrafted and grown can be examined. In fact, human albumin concentration in the blood is well correlated with cholinesterase activity in the blood in the mouse into which human liver cells have been transplanted.

The human liver constructed in a transgenic vertebrate comprising human liver cells transplanted therein can be extracted therefrom and subjected to screening and the like. With the use of the transgenic vertebrate comprising human liver cells transplanted therein and the extracted human liver, screening can be performed in vivo and in vitro.

When the anti-human IL-6 antibody is further administered to a transgenic non-human vertebrate comprising human liver cells transplanted therein in the presence of human IL-6 in vivo, human liver cells grow faster in vivo, compared with the case in which the antibody is not administered. By administration of the anti-human IL-6 antibody to the transgenic non-human vertebrate comprising human liver cells transplanted therein, specifically, engraftment and growth of the transplanted human liver cells can be accelerated. This may be realized because the anti-IL-6 antibody serves as a human IL-6 carrier protein in a non-human vertebrate in which human IL-6 is present and functions for a long period of time by protecting human IL-6 from degradation. A monoclonal antibody or a polyclonal antibody may be used, with a polyclonal antibody being preferable. The anti-human IL-6 antibody may be administered in an amount of, for example, several g to several hundred g per animal. When a non-human vertebrate is a mouse, the anti-human IL-6 antibody may be administered in an amount of 1 μg to 100 g, preferably 2 μg to 20 g, more preferably 2 μg to 10 μg, and particularly preferably 2 μg to 5 μg per mouse.

The present invention also encompasses a method for producing a transgenic non-human vertebrate comprising human liver cells transplanted therein comprising transplanting human liver cells in a non-human vertebrate that has impaired or lowered immune reactions against humans in the presence of human IL-6 in vivo and further administering anti-human IL-6 thereto.

EXAMPLES

The present invention is described in greater detail with reference to the following examples, although the present invention is not limited to these examples.

[Example 1] Growth of Human Liver Cells in TK-NOG-IL-6 Mice

An example in which human liver cells transplanted into mice were grown to a significant extent with the use of human interleukin 6/TK-NOG double transgenic mice (TK-NOG-IL-6 mice) is demonstrated.

The human interleukin 6 (human IL-6) gene expression unit is as described in PMID: 29456539, Hanazawa A., Ito R., Katano I., Kawai K., Goto M., Suemizu H., Kawakami Y., Ito M., and Takahashi T., 2018, Generation of Human Immunosuppressive Myeloid Cell Populations in Human Interleukin-6 Transgenic NOG Mice, Front Immunol., 9, 152 (FIG. 1). Specifically, a DNA fragment comprising human IL-6 cDNA, expression of which is regulated by the human cytomegalovirus (CMV) immediate early enhancer and promoter, was microinjected into a fertilized egg obtained by mating a female NOD mouse and a male NOG mouse to obtain a human IL-6 transgenic founder mouse. The human IL-6 transgenic founder mouse was subjected to mating with a NOG mouse to obtain the scid-IL2Rg$^{null}$ mutant mouse. The established mouse lineage is officially represented by a gene symbol: NOD.Cg-Prkdc$^{scid}$ Il2rg$^{tm1Sug}$ Tg (CMV-IL-6)/ShiJic, which is abbreviated to as "NOG-IL-6." Among the offspring mice resulting from mating between a NOG-IL-6 mouse and a TK-NOG mouse, mice that carry both the human interleukin-6 transgene and the HSVtk transgene are represented by a gene symbol: NOD.Cg-Prkdc$^{scid}$ Il2rg$^{tm1Sug}$ Tg ((Alb-UL23)7-2, CMV-IL-6)/ShiJic, which is abbreviated to as "TK-NOG-IL-6" mice.

Induction of Liver Injury

Ganciclovir (GCV) sodium (Denosine-IV; Mitsubishi Tanabe Pharma) dissolved in distilled water was administered intraperitoneally to mice once or two times in total every other day. As an alternative to GCV, valganciclovir (ValGCV) (valganciclovir hydrochloride; Sigma-Aldrich, Merck) was dissolved in water, and the resulting solution was administered orally to mice. An extent of liver injury was examined via a biochemical serological test and pathological analysis. Blood samples were collected in heparin 1 week after administration of GCV or ValGCV, blood plasma was separated therefrom, and clinical chemical analysis (alanine amino transferase; ALT) was then performed using FUJI DRI-CHEM7000 (Fujifilm).

Transplantation of Human Liver Cells

Commercially available frozen human liver cells (Biopredic, 31-year-old male, LHum170003; Lonza, 35-year-old, HUM4122B) were used as donor cells. The human liver cells were transplanted into TK-NOG-IL-6 and TK-NOG in the manner described below. Adult TK-NOG-IL-6 mice and TK-NOG recipient mice (6- to 8-week-old) were allowed to drink a ValGCV solution (0.06 to 0.08 mg/ml) for 48 hours, blood samples were collected 1 week after the initiation of administration, and plasma ALT levels were then measured. Mice with the plasma ALT value of 600 U/1 or higher were designated as recipient mice of human liver cell transplantation. The human liver cell count and the viability thereof were determined using a hematocytometer by the trypan blue exclusion method. Viable liver cells (approximately $1 \times 10^6$ cells) floated in 40 μl of William's E medium were administered to the spleens using a glass syringe with a 29-gauge needle for subcutaneous insulin administration (Myjector).

Measurement of Human Albumin

A small amount of blood was collected from the venous plexus on the ocular fundus using a polyethylene tube every week starting from 1 week after human liver cell transplantation. The collected blood was diluted to 5,000- to 250,000-fold using tris-buffered saline (TBS) containing 1% bovine serum albumin/0.05% Tween 20, and human albumin concentration was measured using the human albumin ELISA Quantitation Kit (Bethyl Laboratories). The threshold of concentration was 0.016 mg/ml.

Histology and Immunohistochemistry

The liver grafts were fixed with formalin, embedded in paraffin, prepared into 5-μm-thick sections, and subjected to hematoxylin&eosin staining. Sections subjected to immunohistochemical staining were introduced into a target retrieval solution (0.1 M citrate buffer, pH 6.0; 1 mM EDTA, pH 9.0), autoclaved for 10 minutes, and then allowed to stand at room temperature for 20 minutes. Mouse anti-human HLA-class I-A, B, C monoclonal antibodies (clones EMR 8-5; Hokudo) were used as primary antibodies. Mouse Ig was visualized using an amino acid polymer/peroxidase complex-labeled antibody (Histofine Simple Stain Mouse MAX PO (M); Nichirei Bioscience) and a diaminobenzidine (DAB; Dojindo Laboratories) substrate (0.2 mg/ml 3,3-diaminobenzidine tetrahydrochloride, 0.05 M Tris-HCl, pH 7.6, and 0.005% $H_2O_2$) for bright-field immunohistochemical analysis. The sections were counter-stained using hematoxylin. Images were obtained using an upright microscope equipped with AxioCam HRm and AxioCam MRc5 CCD cameras (Carl Zeiss) (Axio Imager, Carl Zeiss).

Isolation and Purification of Human Liver Cells

Liver cells were isolated from TK-NOG-IL-6 mice 5 weeks after human liver cell transplantation via a two-step collagenase perfusion procedure. Briefly, a 27-G butterfly needle was inserted into the postcaval vein, the needle was fixed with an adhesive, and the portal vein was then cut. Subsequently, the liver was perfused with a 1× liver perfusion medium (Thermo Fisher Scientific) at 37° C. for 7 minutes (6 ml/min). The perfusion medium was then exchanged with a 0.15% collagenase medium (360 U/ml type IV collagenase (CLSS4; Worthington Biochemical Corporation, Lakewood, New Jersey, U.S.A.), 140 U/type IV collagenase (C1889; Sigma-Aldrich)/ml, 0.6 mg/ml $CaCl_2$, 10 mM HEPES (pH 7.4), and 10 mg/ml gentamicin), and the liver was perfused at 1.5 ml/min for 10 minutes. The liver was removed therefrom, transferred to a culture dish containing 50 ml of a phosphate buffered solution (PBS) containing 1% fetal bovine serum (FBS; Thermo Fisher Scientific), and mildly shaken to disperse cells from the liver digested with collagenase. The liver cells were filtered through a 100-µm nylon filter and centrifuged at 50×g and 4° C. for 4 minutes. In addition, the cells were washed 2 times with 50 ml of ice-cooed PBS containing 1% FBS. Dead cells were removed via density-gradient centrifugation (60×g for 7 minutes) using 27% Percoll (GE Healthcare, Buckinghamshire, U.K.), and washing with 50 ml of ice-cooled PBS containing 1% FBS at 50× g for 4 minutes was repeated 3 times. Thereafter, the cells were allowed to float in a Dulbecco's modified Eagle medium (DMEM; Sigma-Aldrich) containing 10% FBS, 44 mM NaHCO$_3$, 1 mM sodium pyruvate, and 2 types of antibiotics (50 units/ml penicillin G and 50 g/ml streptomycin; Sigma-Aldrich). The cell count and the viability of the prepared liver cells (Hu-liver cells) were determined by the trypan blue exclusion test.

Flow Cytometric Analysis

The proportion of the human leukocyte antigen (HLA)-expressing human cells and mice H-2kd-expressing mouse cells relative to the total number of the isolated and purified Hu-liver cells was determined via flow cytometric analysis using BD FACSCanto (BD Biosciences). Briefly, cells were stained with the anti-HLA mouse monoclonal antibody (Clone G46-2.6; BD Biosciences) and the anti-mouse H-2kd mouse monoclonal antibody (Clone SF1-1.1; BD Biosciences) and, at the same time, cell viability was evaluated using propidium iodide (BD Biosciences). The data were analyzed using the BD FACSDiva software program (BD Biosciences) and the FlowJo program (Tree Star, San Carlos, CA, U.S.A.). The results are as described below.

Transplantation of Human Liver Cells into TK-NOG-IL-6 Mice (LHum17003 Donor Cells)

Figure 3:
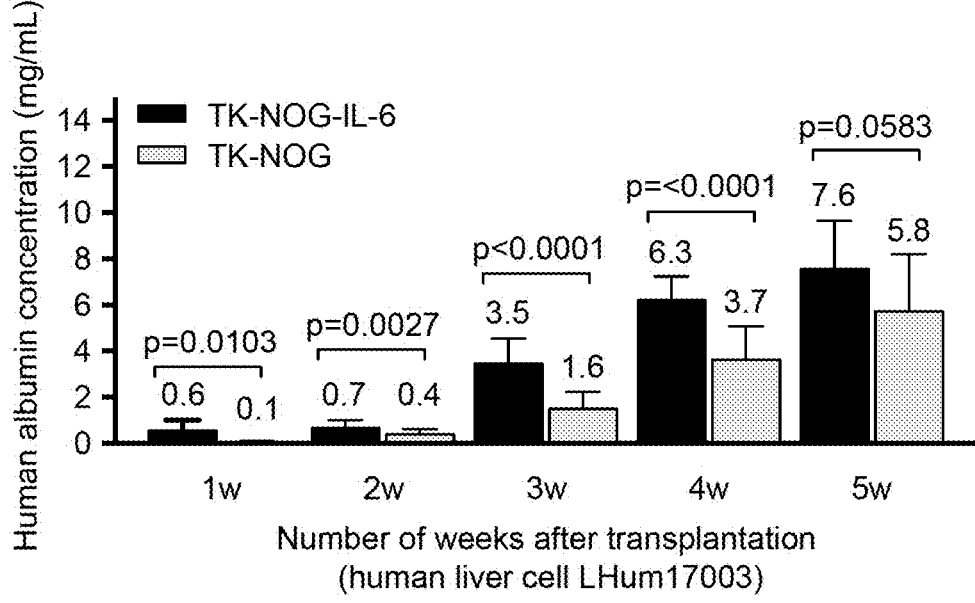
FIG. 3 shows changes in human albumin concentrations in the sera of TK-NOG-IL-6 mice and TK-NOG mice comprising the human liver cells LHum17003 transplanted therein measured with the elapse of time (the average).

The human albumin levels in the sera of TK-NOG-IL-6 mice and TK-NOG mice were measured via ELISA every week starting from 1 week after human liver cell transplantation up to 5 weeks after transplantation. The results are shown in FIG. 3. JP Patent No. 5,073,836 demonstrates that the proportion of the cells replaced with human liver cells in the liver of TK-NOG mice comprising human liver cells transplanted therein (the putative replacement index (RI)); specifically, the human liver cell count, is highly correlated with the human albumin concentration in serum. In addition, Suemizu H. et al., Pest Management Science, 74, 1424, 2018 demonstrates that the proportion of the cells replaced with human liver cells in the liver of TK-NOG mice (the putative replacement index (RI)); specifically, the human liver cell count, is highly correlated with butyl cholinesterase (CHE) activity in serum. The human albumin concentration in the blood of TK-NOG-IL-6 mice was significantly higher than that of TK-NOG mice 1 week after transplantation of liver cells, and the human albumin concentration in the blood of TK-NOG-IL-6 mice was two times higher than that of TK-NOG mice 2 weeks after transplantation. TK-NOG-IL-6 mice still exhibited significantly higher human albumin concentration in the blood, compared with TK-NOG mice 3 weeks and 4 weeks after transplantation. While TK-NOG-IL-6 mice still exhibited high human albumin concentration in the blood 5 weeks after transplantation, there was no significant difference in human albumin concentration between TK-NOG-IL-6 mice and TK-NOG mice. This indicates that the rapid growth of human liver cells reaches a plateau 5 weeks after transplantation.

Figure 4:
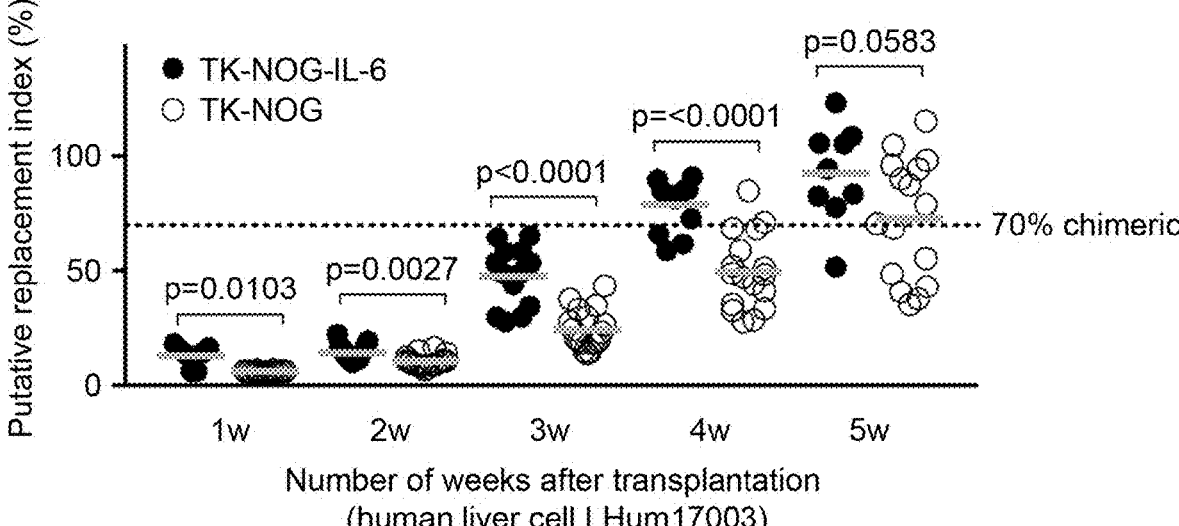
FIG. 4 shows changes in putative replacement indices for TK-NOG-IL-6 mice and TK-NOG mice comprising the human liver cells LHum17003 transplanted therein measured with the elapse of time.

In general, an experiment of drug metabolism involves the use of mice that carry human liver cells exhibiting the putative replacement index of 70% or higher. FIG. 4 shows the blood human albumin concentration of each mouse comprising human liver cells transplanted therein. While a majority of TK-NOG-IL-6 mice comprising human liver cells transplanted therein (10 out of 13 mice, 76.9%) exhibited the replacement index of higher than 70% 4 weeks after transplantation, only a very small number of mice carrying human liver cells (TK-NOG mice) exhibited the replacement index of higher than 70% (2 out of 17 mice, 11.8%). While 9 out of 16 TK-NOG mice (56.2%) exhibited the replacement index of higher than 70% 5 weeks after transplantation, 8 out of 9 TK-NOG-IL-6 mice (88.9%) exhibited the replacement index of higher than 70%. On the basis thereof, it is deduced that the growth rate of the human liver cells transplanted into TK-NOG-IL-6 can be increased and that mice that carry human liver cells exhibiting the replacement index of 70% or higher can be obtained with high efficiency.

Figure 6:
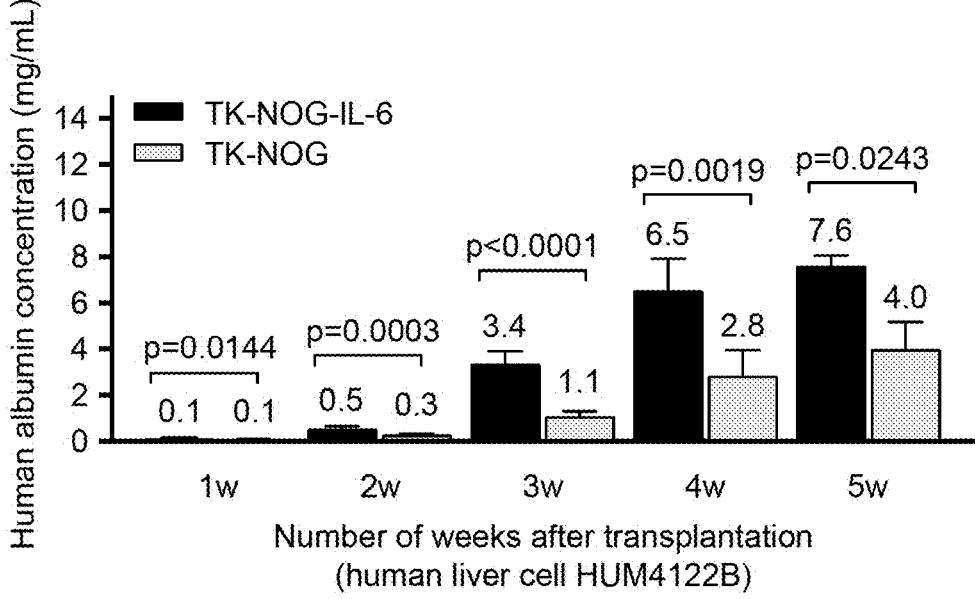
FIG. 6 shows the average human albumin concentration in the sera of TK-NOG-IL-6 mice and TK-NOG mice comprising human liver cells HUM4122B transplanted therein measured with the elapse of time.

Transplantation of human liver cells into TK-NOG-IL-6 mice (HUM4122B donor cells) The human albumin levels in the sera of TK-NOG-IL-6 mice and TK-NOG mice were measured via ELISA every week starting from 1 week after human liver cell transplantation up to 5 weeks after transplantation. The results are shown in FIG. 6. JP Patent No. 5,073,836 demonstrates that the proportion of the cells replaced with human liver cells in the liver of TK-NOG mice comprising human liver cells transplanted therein (the putative replacement index (RI)); specifically, the human liver cell count, is highly correlated with the human albumin concentration in serum. The human albumin concentration in the blood of TK-NOG-IL-6 mice was compared with that of TK-NOG mice during the period from human liver cell transplantation to 5 weeks after transplantation. The results demonstrate that TK-NOG-IL-6 mice constantly exhibit a significantly high human albumin concentration, which is 3 times higher than that of TK-NOG mice, 3 weeks after human liver cell transplantation. The TK-NOG-IL-6 mice exhibited significantly higher human albumin concentration than that of TK-NOG mice 4 and 5 weeks after transplantation.

Figure 7:
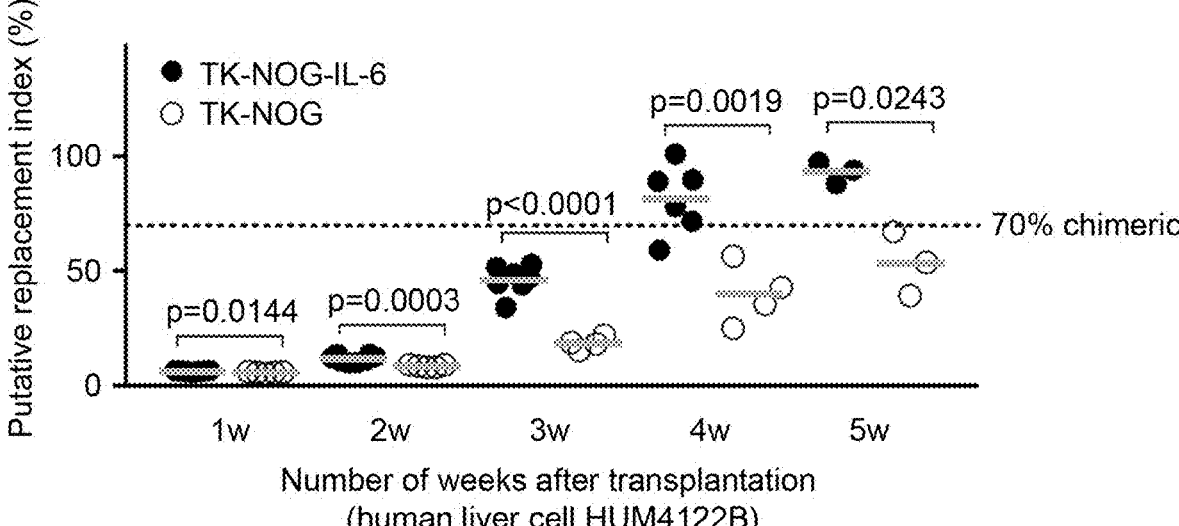
FIG. 7 shows the putative replacement indices for the TK-NOG-IL-6 mice and TK-NOG mice comprising human liver cells HUM4122B transplanted therein measured with the elapse of time.

In general, an experiment of drug metabolism involves the use of mice that carry human liver cells exhibiting the putative replacement index of 70% or higher. FIG. 7 shows the blood human albumin concentration of each mouse comprising human liver cells transplanted therein. While a majority of TK-NOG-IL-6 mice comprising human liver cells transplanted therein (5 out of 6 mice, 82.3%) exhibited the replacement index of higher than 70% 4 weeks after transplantation, no mice carrying human liver cells (TK-NOG mice) exhibited the replacement index of higher than 70% (0 out of 4 mice, 0.0%) While 0 out of 3 TK-NOG mice (0.0%) exhibited the replacement index of higher than 70%, 3 out of 3 TK-NOG-IL-6 mice (100%) exhibited the replacement index of higher than 70%. The results demonstrate that the growth rate of the human liver cells transplanted into TK-NOG-IL-6 can be increased and that the cells with low viability can efficiently survive in TK-NOG mice. Specifically, cells selected from an extensive range of lots can be used, and mice that carry human liver cells exhibiting the replacement index of 70% or higher can be obtained with high efficiency.

Figure 5:
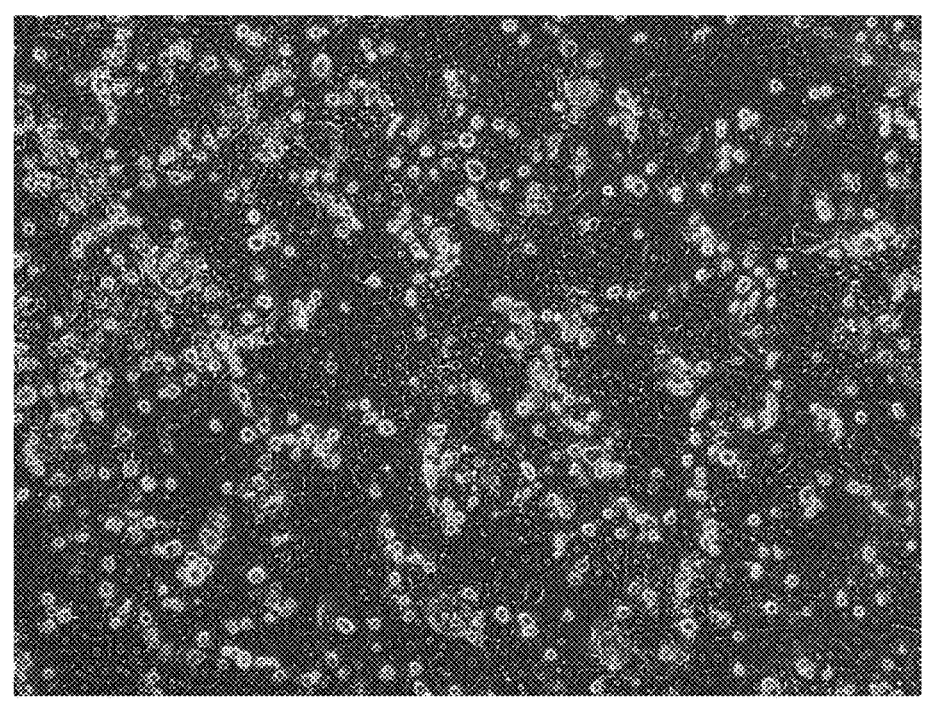
FIG. 5 shows forms of liver cells 48 hours after seeding of liver cells isolated and purified from the TK-NOG-IL-6 mice comprising human liver cells transplanted therein in a type I collagen-coated dish.
Figure 8:
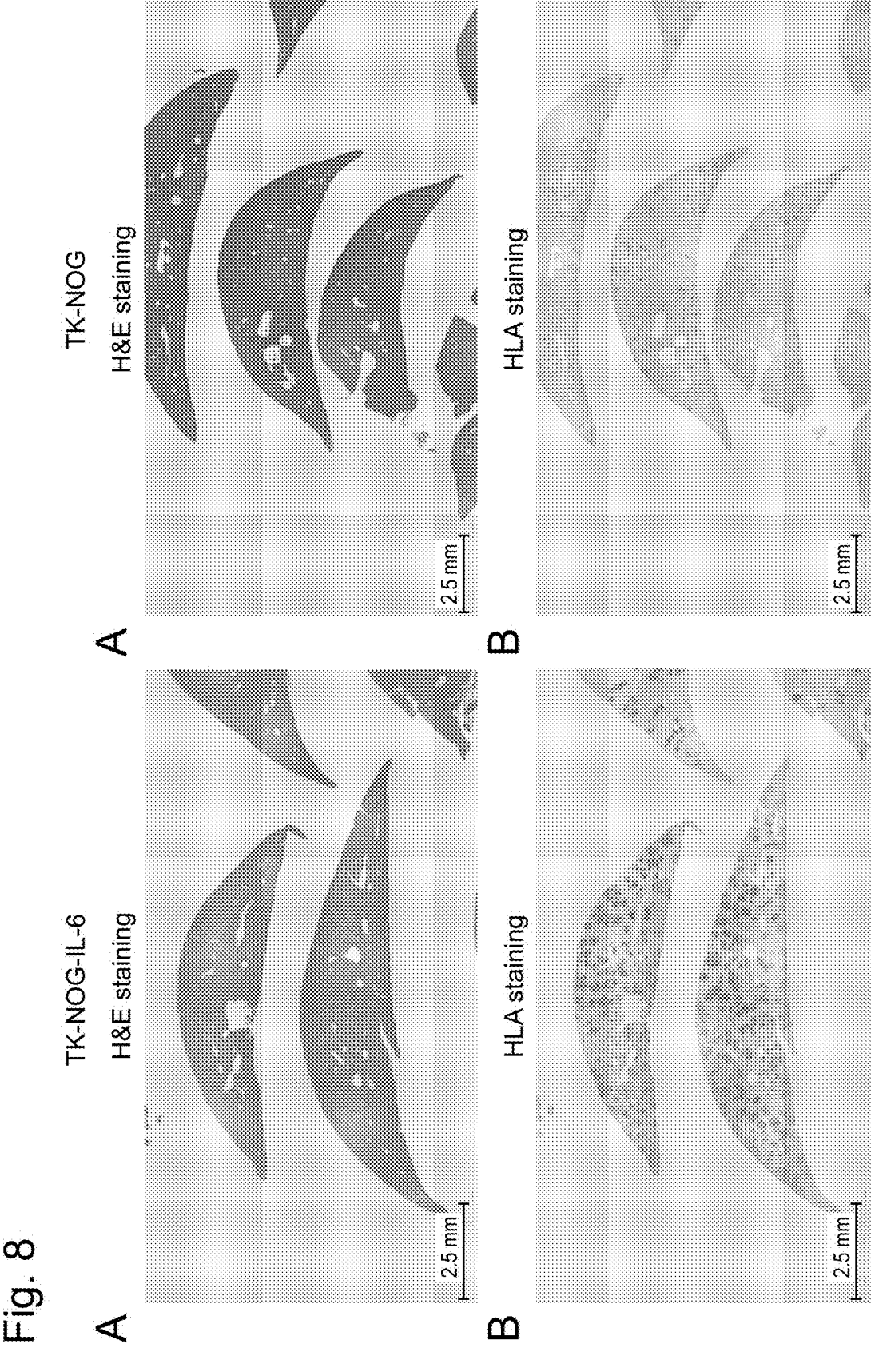
FIG. 8 shows the results of staining of the TK-NOG-IL-6 mice and the TK-NOG mice 2 weeks after transplantation of LHum17003 donor cells (A: H&E staining; B: HLA staining).
Figure 9:
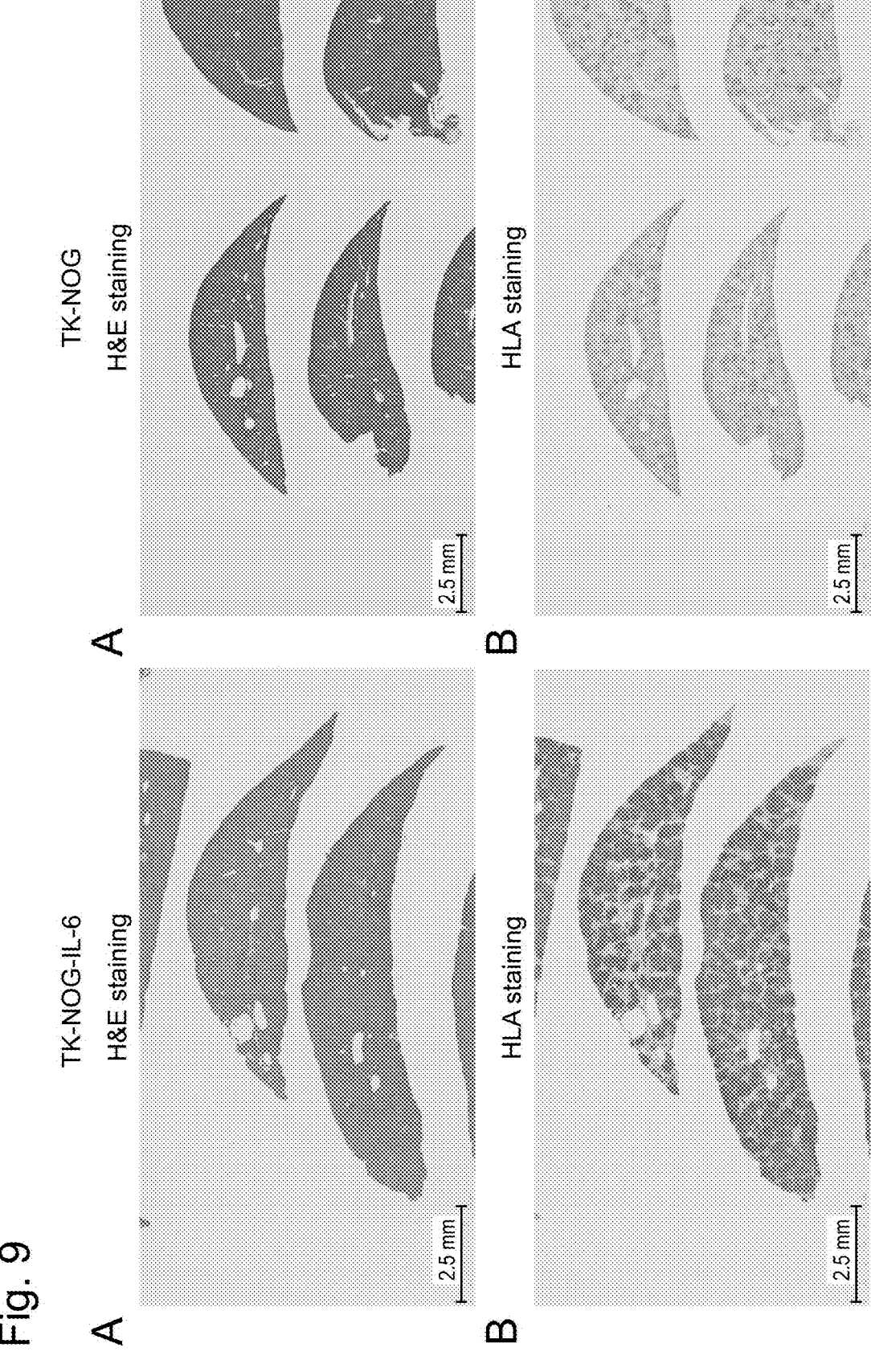
FIG. 9 shows the results of staining of the TK-NOG-IL-6 mice and the TK-NOG mice 3 weeks after transplantation of LHum17003 donor cells (A: H&E staining; B: HLA staining).
Figure 10:
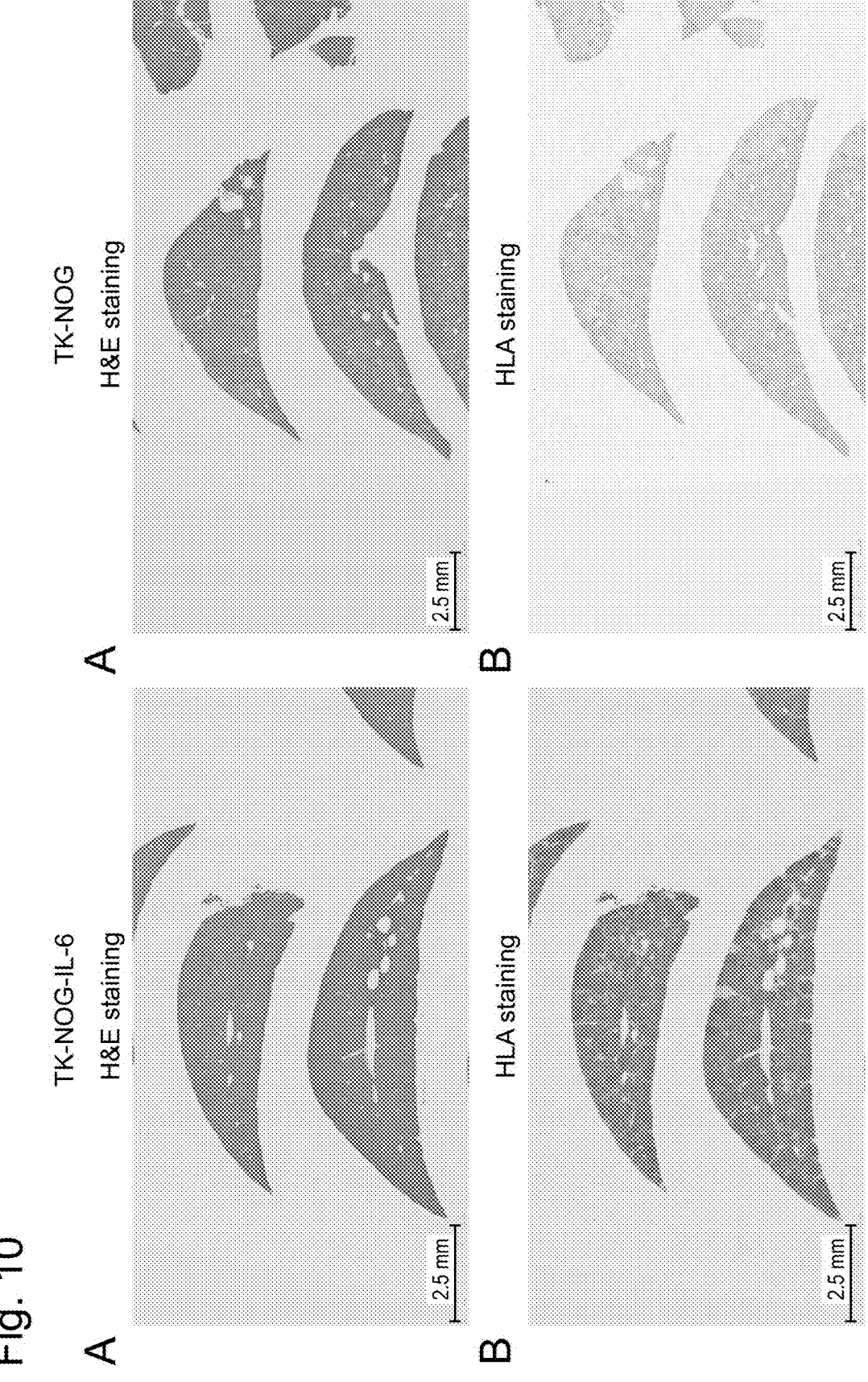
FIG. 10 shows the results of staining of the TK-NOG-IL-6 mice and the TK-NOG mice 4 weeks after transplantation of LHum17003 donor cells (A: H&E staining; B: HLA staining).
Figure 11:
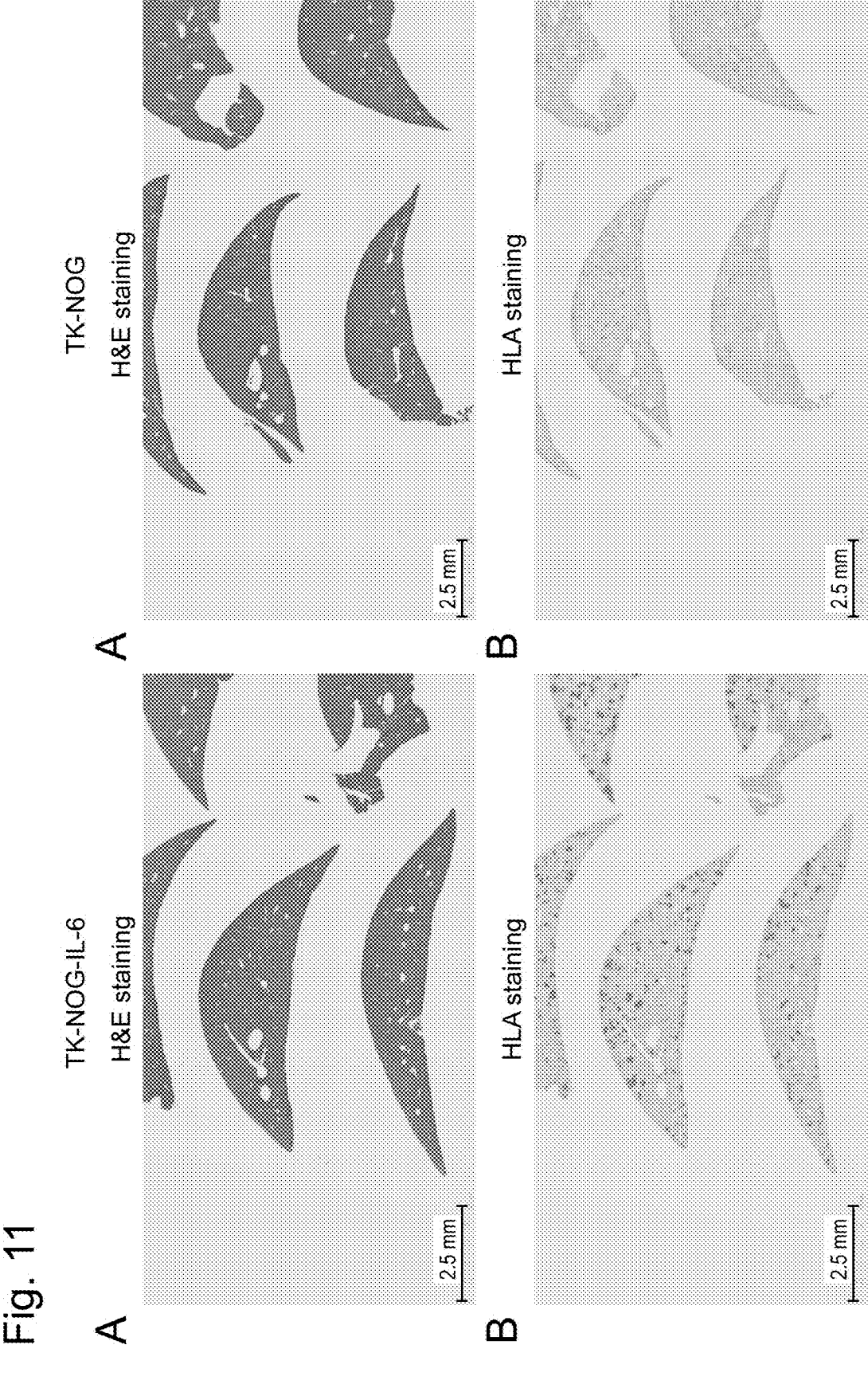
FIG. 11 shows the results of staining of the TK-NOG-IL-6 mice and the TK-NOG mice 2 weeks after transplantation of HUM4122B donor cells (A: H&E staining; B: HLA staining).
Figure 12:
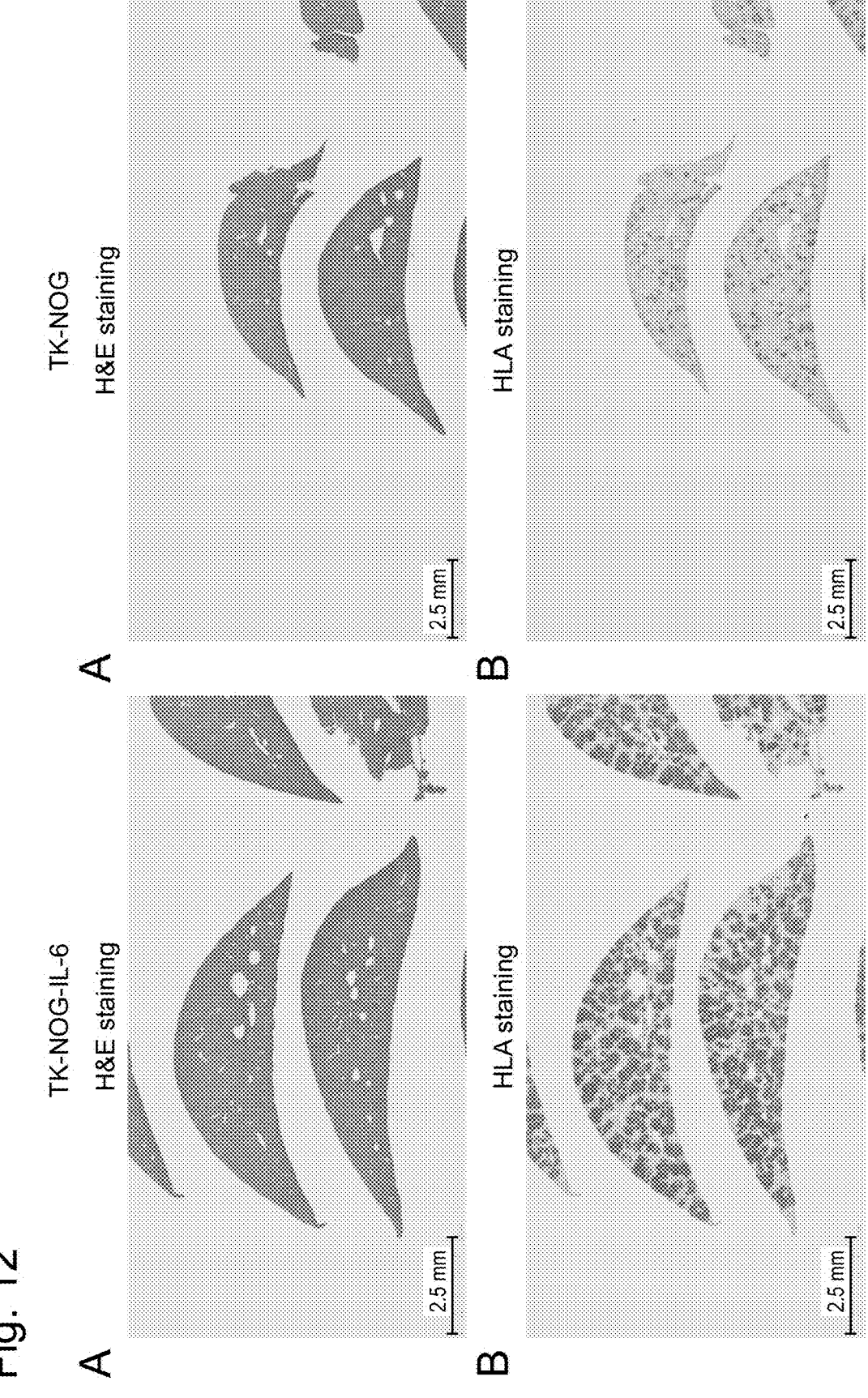
FIG. 12 shows the results of staining of the TK-NOG-IL-6 mice and the TK-NOG mice 3 weeks after transplantation of HUM4122B donor cells (A: H&E staining; B: HLA staining).
Figure 13:
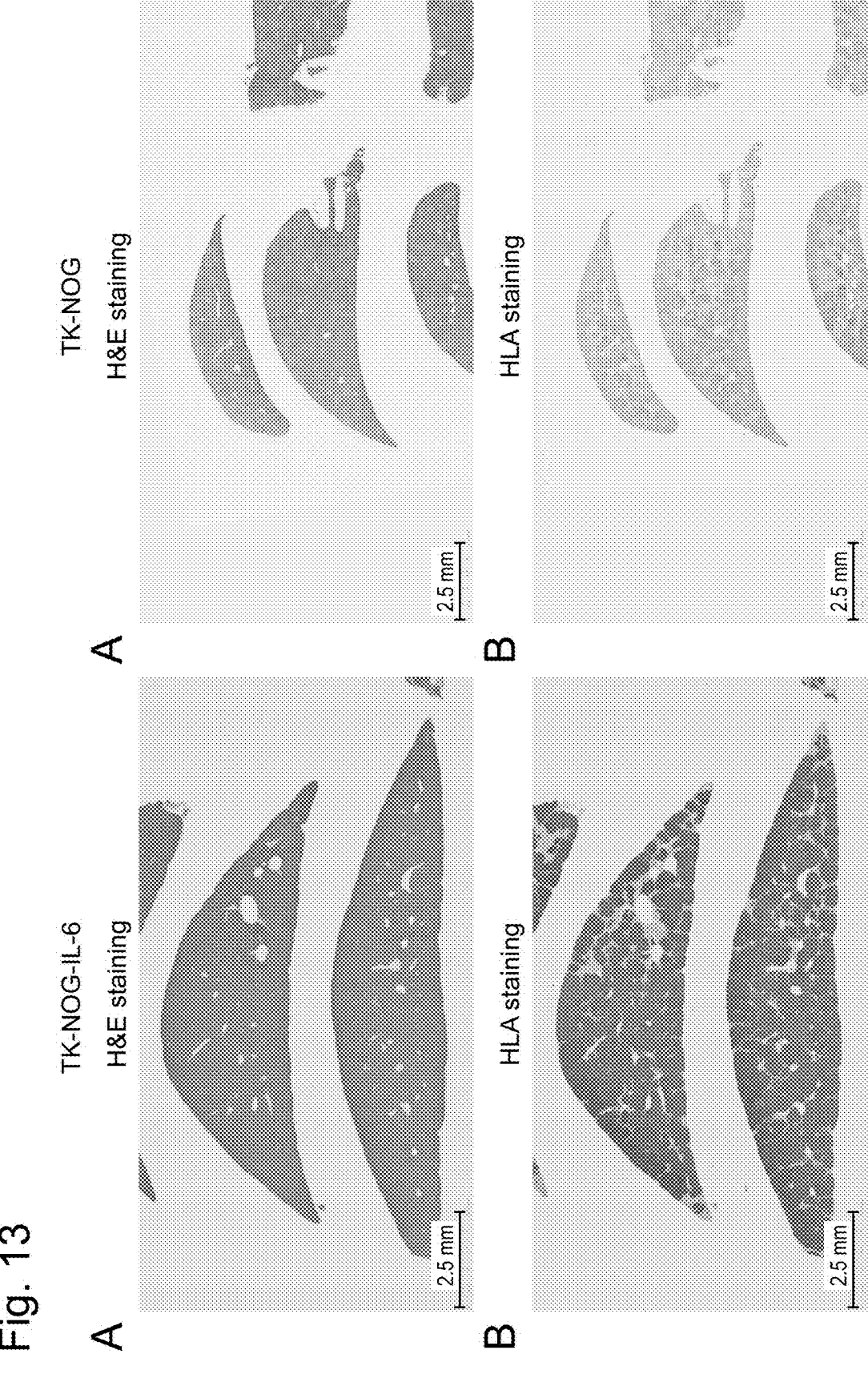
FIG. 13 shows the results of staining of the TK-NOG-IL-6 mice and the TK-NOG mice 4 weeks after transplantation of HUM4122B donor cells (A: H&E staining; B: HLA staining).
Figure 14:
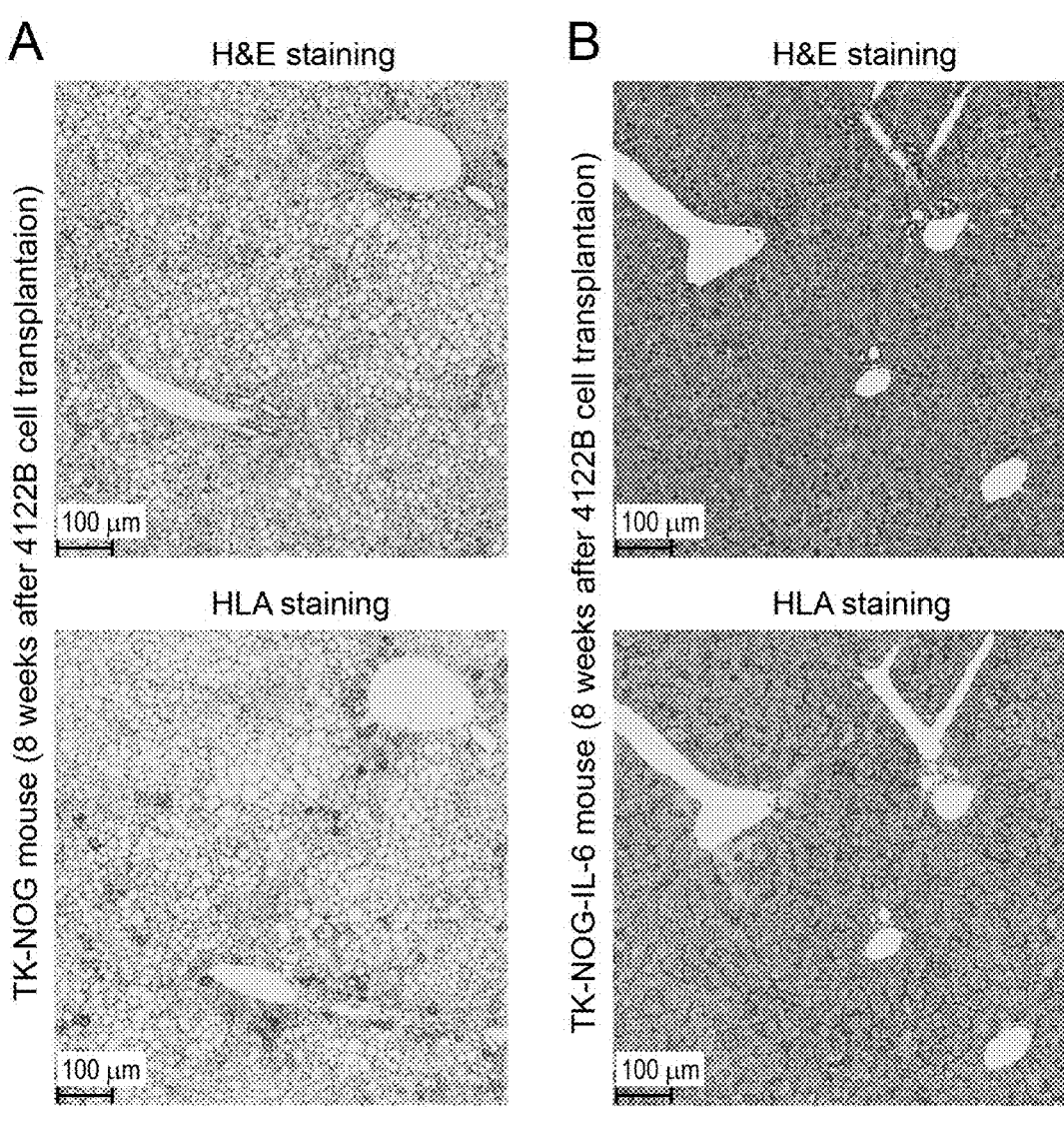
FIG. 14 shows liver tissue images of the TK-NOG-IL-6 mice (A) and of the TK-NOG mice (B) 8 weeks after transplantation (H&E staining and HLA staining).

The results of histological and immunohistochemical analyses of the livers of TK-NOG-IL-6 mice obtained 2, 3, and 4 weeks after transplantation of human liver cells are shown. Continuous sections are stained with H&E and the human leukocyte antigen (HLA), and the results of staining are shown in FIGS. 8 to 13. FIG. 8 shows the results of staining of the TK-NOG-IL-6 mice and the TK-NOG mice 2 weeks after transplantation of LHum17003 donor cells, FIG. 9 shows the results of staining 3 weeks after transplantation, and FIG. 10 shows the results of staining 4 weeks after transplantation. Most human liver cells were present as large-size foci in the host liver tissue 2 weeks after transplantation (FIG. 8). Three weeks after transplantation, large colonies of human liver cell foci conjugated to constitute a half or more of the host liver tissue (FIG. 9). In addition, the replacement index with human liver cells that is deduced based on the serum human albumin concentration was higher than 70% 4 weeks after transplantation, large foci observed up to 3 weeks after transplantation disappeared, and most of the host liver tissue was replaced with human liver cells (FIG. 10). FIG. 11 shows the results of staining of the TK-NOG-IL-6 mice and the TK-NOG mice 2 weeks after transplantation of HUM4122B donor cells, FIG. 12 shows the results of staining 3 weeks after transplantation, and FIG. 13 shows the results of staining 4 weeks after transplantation. Most human liver cells were present as large foci in the host liver tissue 2 weeks after transplantation (FIG. 11). Three weeks after transplantation, large colonies of human liver cell foci conjugated to constitute a half or more of the host liver tissue (FIG. 12). In addition, the replacement index with human liver cells that is deduced based on the serum human albumin concentration was higher than 70% 4 weeks after transplantation, large foci observed up to 3 weeks after transplantation disappeared, and most of the host liver tissue was replaced with human liver cells (FIG. 13). FIG. 14 shows liver tissue images of the human liver cells had rapidly grown up to 5 weeks after transplantation by a two-step collagenase perfusion procedure. Table 1 shows the information when liver cells were isolated and purified from TK-NOG-IL-6 mice after transplantation of human liver cells. The number of collected liver cells was as high as $3.9 \times 10^7$ on average per mouse, and the average viability was as high as 90.8%. While human cell positive selection or mouse cell negative selection were not performed, the percentage of mouse cell inclusion was 2.3% on average, and the percentage of human cell inclusion was 94.4% on average. That is, human cells were dominant to a significant extent. FIG. 5 shows forms of liver cells 48 hours after seeding of liver cells in a type I collagen-coated dish. Polygonal cells formed a cobblestone sheet, many binuclear cells characteristic of liver cells were observed, and a configuration similar to that of normal human liver cells was observed.

The number of cells transplanted into a mouse was $0.1 \times 10^7$, and the number of cells collected was approximately $4 \times 10^7$. This indicates that the present invention provides an innovative technique that enables proliferation of human liver cells, which cannot be proliferated in vitro, by 40 times within 5 weeks. In the past, it was impossible to provide fresh human liver cells in a systematic manner with the use of human clinical materials that cannot be obtained on a regular basis. Use of the animal prepared in the present invention as a liver cell resource to be provided for in vitro research enables on-demand provision of fresh human liver cells in a systematic manner.

TABLE 1

Isolation of liver cells from TK-NOG-IL-6 chimeric mouse with human liver

| Human liver cells used for transplantation | | | | | | TK-NOG-IL-6 chimeric mouse with human liver | | | | | | | | | Isolated liver cells | | | Number of cells |
| Name | Race | Age | Sexuality | Num-ber | Sex-uality | Number of days after trans-plantation | Body weight (g) | ALT (U/L) | CHE (U/L) | hALB (mg/mL) | Total cell count ($\times 10^7$) | Via-bility (%) | Proportion (%) Mouse[1] | Proportion (%) Human[2] | collected per body weight (cells/g BW) |
| --- | --- | --- | --- | --- | --- | --- | --- | --- | --- | --- | --- | --- | --- | --- | --- |
| LHum 17003 | African American | 31 | Male | #6 | Female | 28 | 12.1 | 400 | 205 | 5.5 | 3.75 | 93.8 | 3.0 | 93.7 | $0.31 \times 10^7$ |
| | | | | #22 | Male | 34 | 17.8 | 325 | 175 | 4.4 | 1.95 | 92.8 | 2.2 | 94.6 | $0.11 \times 10^7$ |
| | | | | #26 | Male | 34 | 15.9 | 245 | 275 | 5.8 | 6.00 | 85.7 | 1.8 | 95.0 | $0.38 \times 10^7$ |
| | | | | | Average | 32.0 | 15.3 | 323.3 | 218.3 | 5.2 | 3.90 | 90.8 | 2.3 | 94.4 | $0.27 \times 10^7$ |

[1]Proportion of anti-mouse H-2kd antibody-positive cells in the isolated liver cells
[2]Proportion of anti-human HLA antibody-positive cells in the isolated liver cells
ALT: alanine aminotransferase;
CHE: cholinesterase;
hALB: human albumin TK-NOG-IL-6 mice and of the TK-NOG mice 8 weeks after transplantation. While the growth of human liver cells without gaps and air bubbles in many human liver cells are observed via H&E staining of liver tissue of TK-NOG mice, a cord-like structure is observed in the hepatic lobule via H&E staining of liver tissue of TK-NOG-IL-6 mice, and a portal triad composed of the interlobular artery, the interlobular vein, and the interlobular bile duct is very similar to that of humans.

Whether or not mice carrying human liver cells with a high replacement index, which can be prepared within a short period of time with the use of TK-NOG-IL-6 mice, are useful as liver cell resources to be provided for in vitro research was examined. Specifically, liver cells were isolated from 3 TK-NOG-IL-6 mice in which the transplanted Whether or not mice carrying human liver cells with a high replacement index, which can be prepared within a short period of time with the use of TK-NOG-IL-6 mice, are useful as liver cell resources to be provided for in vitro research was further examined. Specifically, liver cells were isolated from 43 TK-NOG-IL-6 mice in which the transplanted human liver cells (Biopredic: 31-year-old male LHum170003, 5-year-old male LHum170003; Lonza: 30-year-old female HUM4119F, 0.9-year-old male HUM4282, 12-year-old female HUM181001B) had rapidly grown up to 5 weeks after transplantation by a two-step collagenase perfusion procedure. Table 2 shows the information (representative 5 examples) when liver cells were isolated and purified from TK-NOG-IL-6 mice after transplantation of human liver cells. The average number of liver cells collected from 43 mice was as high as $11.7 \times 10^7$ per mouse, and the average viability was as high as 87.8%. While human cell positive selection or mouse cell negative selection were not performed, the percentage of mouse cell inclusion was 2.9% on average, and the percentage of human cell inclusion was 95.3% on average. That is, human cells were dominant to a significant extent.

The number of cells transplanted into a mouse was $0.03 \times 10^7$, and the number of cells collected was approximately $11.6 \times 10^7$. This indicates that the present invention provides an innovative technique that enables proliferation of human liver cells, which cannot be proliferated in vitro, by 370 times within 5 weeks.

UL23 mutant 30), CMV-IL-6)/ShiJic, which is abbreviated to as "TKmut30-NOG-IL-6 mice."

Induction of Liver Injury

A solution of valganciclovir (ValGCV) (valganciclovir hydrochloride; Sigma-Aldrich, Merck) dissolved in distilled water at 0.05 to 0.5 mg/ml was administered orally to mice by allowing the mice to freely drink the solution for 24 to 72 hours. As an alternative to ValGCV, ganciclovir (GCV) sodium (Denosine-IV; Mitsubishi Tanabe Pharma) was administered intraperitoneally to mice once or two times in total every other day. An extent of liver injury was examined via a biochemical serological test and pathological analysis. Blood samples were collected in heparin 1 week after

TABLE 2

Isolation of liver cells from TK-NOG-IL-6 chimeric mouse with human liver

| Human liver cells used for transplantation | | | | Num-ber | TK-NOG-IL-6 chimeric mouse with human liver | | | | | Isolated liver cells | | | | |
|---|---|---|---|---|---|---|---|---|---|---|---|---|---|---|
| | | | | | | Number of days after trans- | Body weight | CHE | hALB (mg/ | Total cell count | Viability | Proportion (%) | | Number of cells collected per body weight (cells/ |
| Name | Race | Age | Sexuality | | Sexuality | plantation | (g) | (U/L) | mL) | $(\times 10^7)$ | (%) | Mouse[1] | Human[2] | g BW) |
| HUM4119F | African American | 30 | Female | #1 | Female | 35 | 13.1 | 277 | 6.6 | | | | | 8.9 |
| HUM4282 | Hispanic | 0.9 | Male | #22 | Male | 35 | 15.6 | 297 | 6.8 | 14.0 | 91.6 | 1.3 | 97.5 | 9.0 |
| HUM181001B | Caucasian | 12 | Female | #49 | Male | 34 | 14.8 | 272 | 9.5 | 13.0 | 89.2 | 1.4 | 97.9 | 8.8 |
| HEP187266 | Caucasian | 5 | Male | #27 | Male | 35 | 21.5 | 222 | 2.8 | 13.4 | 84.8 | 3.1 | 94.9 | 6.2 |
| LHum17003 | African American | 31 | Male | #26 | Male | 34 | 15.9 | 275 | 5.8 | 6.0 | 85.7 | 1.8 | 94.9 | 3.8 |
| | | | | | Average | 34.6 | 16.18 | 268.6 | 6.3 | 11.60 | 87.8 | 2.1 | 96.3 | 7.3 |

[1]Proportion of anti-mouse H-2kd antibody-positive cells in the isolated liver cells
[2]Proportion of anti-human HLA antibody-positive cells in the isolated liver cells
CHE: cholinesterase;
hAlB: human albumin Transplantation of Human Liver Cells into TKmut30-NOG-IL-6 Mice (LHum17003 Donor Cells) An example in which human liver cells transplanted into mice were grown to a significant extent with the use of double transgenic mice (TKmut-NOG-IL-6 mice) of TKmut30-NOG mice comprising TK mutant 30, which is a mutant of the human herpes simplex virus type 1-thymidine kinase (HSV-tk) gene, under the control of the transthyretin promoter and human interleukin-6 is demonstrated.

Figure 2:
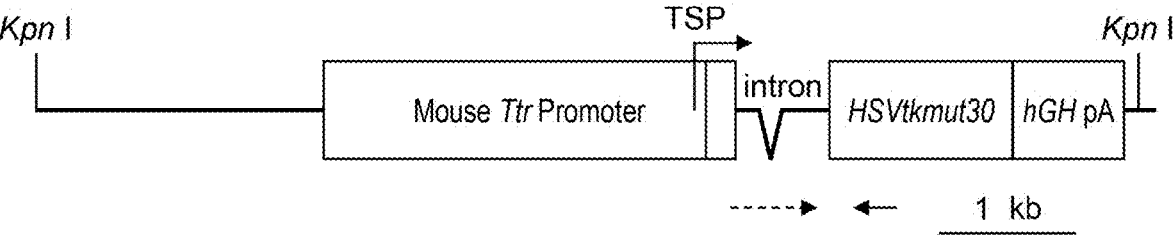
FIG. 2 shows a structure of a HSV-tk mutant 30 (TKmut30) gene expression unit.

With the use of the human herpes simplex virus type 1-thymidine kinase gene mutant (HSV-TK mutant 30) expression unit (FIG. 2), a DNA fragment comprising cDNA of HSV-TKmutant 30, expression of which is regulated by the mouse transthyretin gene promoter, was microinjected into a fertilized egg obtained by mating a female NOD mouse and a male NOG mouse to obtain a HSV-TKmutant 30 transgenic founder mouse. The HSV-TKmutant 30 transgenic founder mouse was subjected to mating with a NOG mouse to obtain the scid-IL2Rg$^{null}$ mutant mouse. The established mouse lineage is officially represented by a gene symbol: NOD.Cg-Prkdc$^{scid}$ Il2rg$^{tm1Sug}$ Tg (Ttr-UL23 (common name: tk) mutant 30)/ShiJic, which is abbreviated to as "TKmut30-NOG." Among the offspring mice resulting from mating between a TKmut30-NOG mouse and a NOG-IL-6 mouse, mice that carry both the human interleukin-6 transgene and the HSVtk mutant 30 transgene are represented by a gene symbol: NOD.Cg-Prkdc$^{scid}$ Il2rg$^{tm1Sug}$ Tg ((Ttradministration of GCV or ValGCV, blood plasma was separated therefrom, and clinical chemical analysis (alanine amino transferase; ALT) was then performed using FUJI DRI-CHEM7000 (Fujifilm).

Transplantation of Human Liver Cells

Commercially available frozen human liver cells (Biopredic, 31-year-old male, LHum170003) were used as donor cells. The human liver cells were transplanted into TKmut30-NOG-IL-6 and TKmut30-NOG in the manner described below. Adult TKmut30-NOG-IL-6 and TKmut30-NOG recipient mice (6- to 8-week-old) were allowed to drink a ValGCV solution (0.4 mg/ml) for 72 hours, blood samples were collected 1 week after the initiation of administration, and plasma ALT levels were then measured. Mice with the plasma ALT value of 600 U/l or higher were designated as recipient mice of human liver cell transplantation. The human liver cell count and the viability thereof were determined using a hematocytometer by the trypan blue exclusion method. Viable liver cells (approximately $1 \times 10^6$ cells) floated in 40 l of William's E medium were administered to the spleens using a glass syringe with a 29-gauge needle for subcutaneous insulin administration (Myjector).

Measurement of Human Albumin

A small amount of blood was collected from the venous plexus on the ocular fundus using a polyethylene tube every week starting from 1 week after human liver cell transplantation. The collected blood was diluted to 5,000- to 250,000-fold using tris-buffered saline (TBS) containing 1% bovine serum albumin/0.05% Tween 20, and human albumin concentration was measured using the human albumin ELISA Quantitation Kit (Bethyl Laboratories). The threshold of concentration was 0.016 mg/ml.

Figure 15:
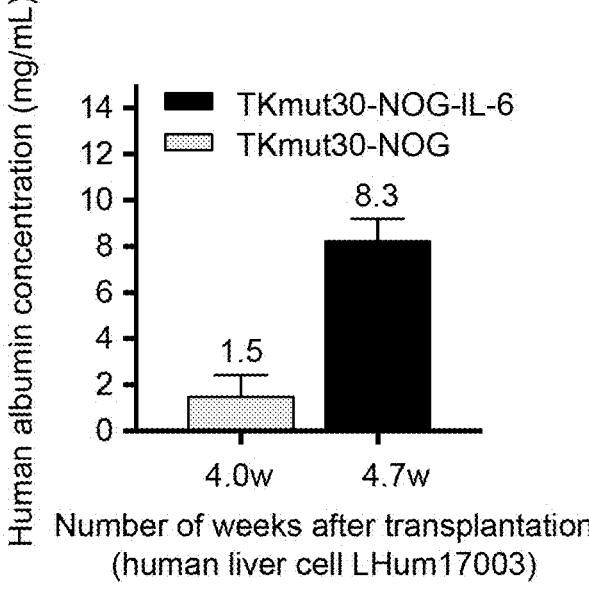
FIG. 15 shows changes in human albumin concentrations in the sera of the TKmut30-NOG-IL-6 mice and the TKmut30-NOG mice comprising the human liver cells LHum17003 transplanted therein measured with the elapse of time.

The human albumin levels in the sera of TKmut30-NOG-IL-6 mice were measured via ELISA 4 weeks after transplantation of human liver cells. The human albumin levels in the sera of TKmut30-NOG mice were measured via ELISA 4.7 weeks after transplantation of human liver cells. The results are shown in FIG. 15. JP Patent No. 5,073,836 demonstrates that the proportion of the cells replaced with human liver cells in the liver of TK-NOG mice comprising human liver cells transplanted therein (the putative replacement index (RI)); specifically, the human liver cell count, is highly correlated with the human albumin concentration in serum. Accordingly, the the human liver cell count should be highly correlated with the human albumin concentration in serum of TKmut30-NOG mice. The human albumin concentration in the blood of TKmut30-NOG-IL-6 mice was compared with that of TKmut-NOG mice up to the time point, which is 5 weeks after human liver cell transplantation. While a significant difference test could not be performed due to a small number of samples, TKmut30-NOG-IL-6 mice exhibited a high percentage of engraftment, which is equivalent to that of TK-NOG-IL-6 and 5 times higher than that of TKmut30-NOG mice.

Figure 16:
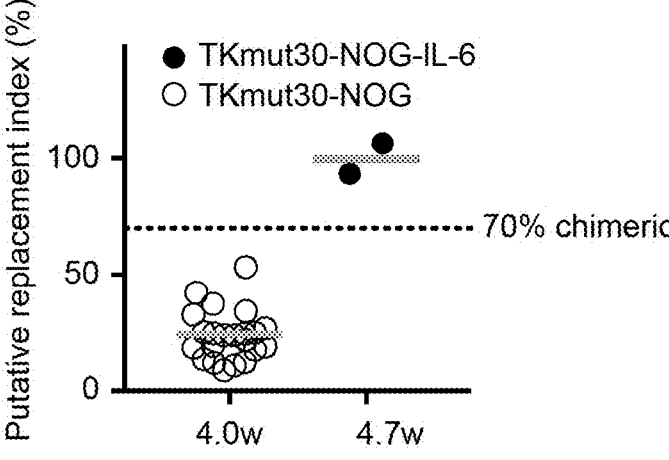
FIG. 16 shows changes in putative replacement indices for the TKmut30-NOG-IL-6 mice and the TKmut30-NOG mice comprising the human liver cells LHum17003 transplanted therein measured with the elapse of time.

In general, an experiment of drug metabolism involves the use of mice that carry human liver cells exhibiting the putative replacement index of 70% or higher (FIG. 16, 70% chimeric). FIG. 16 shows the putative replacement index of each mouse comprising human liver cells transplanted therein. While all the TKmut30-NOG-IL-6 mice comprising human liver cells transplanted therein (2 out of 2 mic, 100%) exhibited the replacement index of higher than 70% 4.7 weeks after transplantation, no TKmut30-NOG mice that would not express human IL-6 exhibited the replacement index of higher than 70% (0 out of 22 mice, 0.0%).

Figure 17:
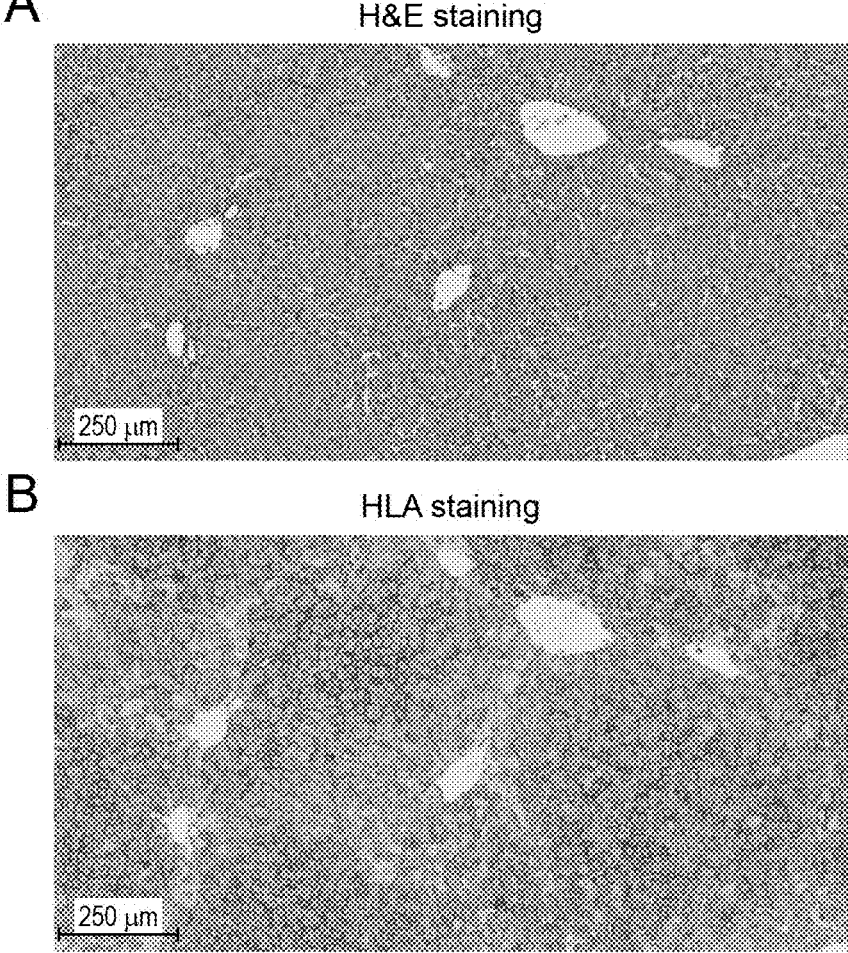
FIG. 17 shows liver tissue images of the TKmut30-NOG-IL-6 mice 7 weeks after transplantation of the human liver cells LHum17003 (A: H&E staining; B: HLA staining).

FIG. 17 shows the results of staining of TKmut30-NOG-IL-6 mice 7 weeks after transplantation of LHum17003 donor cells. Most of host liver tissue was replaced with human liver cells (FIG. 17). In addition to the cord-like structure observed in the hepatic lobule via H&E staining as with the case of TK-NOG-IL-6 mice, a portal triad composed of the interlobular artery, the interlobular vein, and the interlobular bile duct is very similar to that of humans.

Figure 18:
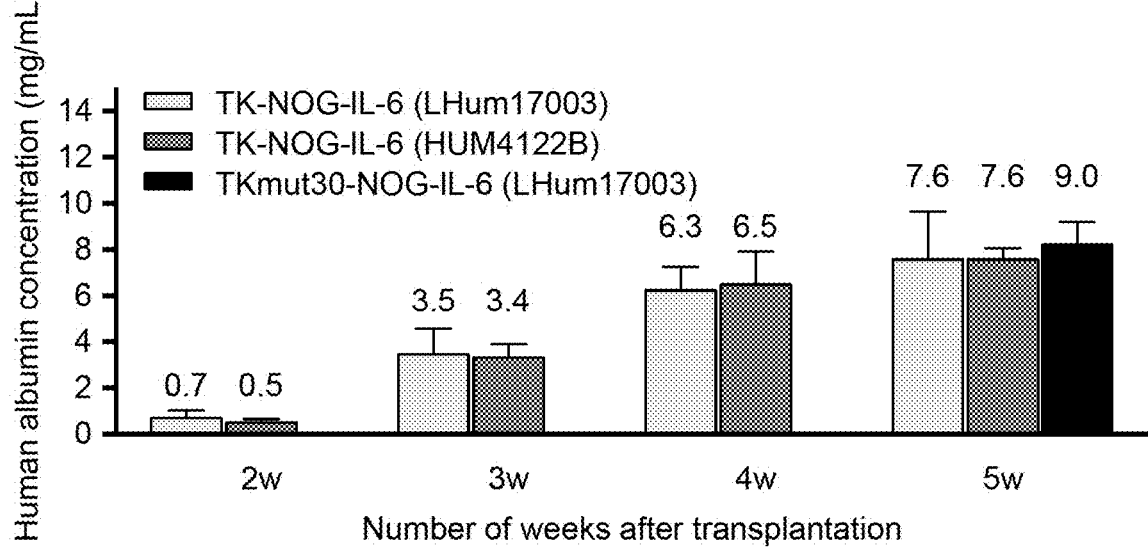
FIG. 18 shows the results of measurement of human albumin concentrations in the sera of the TKmut30-NOG-IL-6 mice and the TK-NOG-IL-6 mice after transplantation of human liver cells.

FIG. 18 shows the results of measurement of human albumin concentrations in the sera of the TKmut30-NOG-IL-6 mice expressing human IL-6 (TKmut30-NOG-IL-6) and TK-NOG mice (TK-NOG-IL-6) via ELISA every week starting from 1 week after human liver cell transplantation to 5 weeks after transplantation. The results of measurement demonstrate that, as with the case of TK-NOG mice, similar effects would be achieved in the human herpes simplex virus type 1-thymidine kinase gene mutant (HSV-TK mutant 30) as the human herpes simplex virus type 1-thymidine kinase gene and in mice in which gene expression of interest would be regulated by the mouse transthyretin gene promoter in the presence of human IL-6. The data on TKmut30-NOG mice were not obtained 2, 3, and 4 weeks after transplantation.

Replacement with human liver cells within such a short period of time is peculiar to mice in which human IL-6 is present, and such replacement is not observed in TK-NOG mice or TKmut30-NOG mice that do not comprise human IL-6 Tg. This demonstrates that human IL-6 has effects of accelerating the growth of human liver cells transplanted in vivo to a significant extent and human IL-6 is useful for accelerating the growth of human liver cells in the bodies of animals other than humans. Animals that carry human liver cells thus produced are useful for not only research of drug metabolism or the liver but also useful as liver cell resources to be provided for in vitro research involving the use of human liver cells.

[Example 2] Measurement of the Doubling Time of Human Liver Cells Transplanted into TK-NOG-IL-6 Mice The growth of the human liver cells transplanted into mice is terminated when the liver is grown to a given size. The time elapsed after the termination of cell growth is not correlated with the number of grown cells. Thus, it is necessary to determine the doubling time before the termination of cell growth, and the minimal doubling time is the maximal growth rate of the cells. Thus, the liver cells were isolated from TK-NOG-IL-6 mice and TK-NOG mice by the method described above at various time points after transplantation of human liver cells, and the cell count and the viability were determined by the trypan blue exclusion method. In addition, the rate of HLA-positive cells (the rate of human cells) was determined via flow cytometric analysis. The doubling time of the human liver cells transplanted into mice was determined in accordance with the equations shown below, the time elapsed after cell transplantation was plotted on the horizontal axis, the doubling time was plotted on the vertical axis, and the minimal doubling time was determined based thereon.

Doubling time(the number of days)=the time after cell transplantation/the frequency of cell division Time after cell transplantation(the number of days) =the date of isolation and collection of liver cells−the date of liver cell transplantation Frequency of cell division(the number of times) =LOG(multiplication factor:2)

Growth rate(doubling)=(the number of collected cells×the HLA positive rate)/the number of transplanted cells 1. Materials and Method
(1) Isolation and Purification of Human Liver Cells Liver cells were isolated from TK-NOG-IL-6 mice and TK-NOG mice at least 7 days after human liver cell transplantation via a two-step collagenase perfusion procedure. Briefly, a 27-G butterfly needle was inserted into the postcaval vein, the needle was fixed with an adhesive, and the portal vein was then cut. Subsequently, the liver was perfused with a 1× liver perfusion medium (Thermo Fisher Scientific) at 37° C. for 7 minutes (6 ml/min). The perfusion medium was then exchanged with a 0.15% collagenase medium (360 U/ml type IV collagenase (CLSS4; Worthington Biochemical Corporation, Lakewood, New Jersey, U.S.A.), 140 U/type IV collagenase (C1889; Sigma-Aldrich)/ml, 0.6 mg/ml $CaCl_2$, 10 mM HEPES (pH 7.4), and 10 mg/ml gentamicin), and the liver was perfused at 1.5 ml/min for 10 minutes. The liver was removed therefrom, transferred to a culture dish containing 50 ml of a phosphate buffered solution (PBS) containing 1% fetal bovine serum (FBS; Thermo Fisher Scientific), and mildly shaken to disperse cells from the liver digested with collagenase. The liver cells were filtered through a 100-μm nylon filter and centrifuged at 50×g and 4° C. for 4 minutes. In addition, the cells were washed 2 times with 50 ml of ice-cooed PBS containing 1% FBS. The cell count and the viability of the prepared liver cells (Hu-liver cells) were determined by the trypan blue exclusion test. When the viability was lower than 70%, dead cells were removed via density-gradient centrifugation (60×g for 7 minutes) using 27% Percoll (GE Healthcare, Buckinghamshire, U.K.), and washing with 50 ml of ice-cooed PBS containing 1% FBS at 50× g for 4 minutes was repeated 3 times. Thereafter, the cells were allowed to float in a Dulbecco's modified Eagle medium (DMEM; Sigma-Aldrich) containing 10% FBS, 44 mM NaHCO$_3$, 1 mM sodium pyruvate, and 2 types of antibiotics (50 units/ml penicillin G and 50 g/ml streptomycin; Sigma-Aldrich). The cell count and the viability of the prepared liver cells (Hu-liver cells) were determined by the trypan blue exclusion test.

(2) Flow Cytometric Analysis

The proportion of the human leukocyte antigen (HLA)-expressing human cells and mice H-2kd-expressing mouse cells relative to the total number of the isolated and purified Hu-liver cells was determined via flow cytometric analysis using BD FACSCanto (BD Biosciences). Briefly, cells were stained with the anti-HLA mouse monoclonal antibody (Clone G46-2.6; BD Biosciences) and the anti-mouse H-2kd mouse monoclonal antibody (Clone SF1-1.1; BD Biosciences) and, at the same time, cell viability was evaluated using propidium iodide (BD Biosciences). The data were analyzed using the BD FACSDiva software program (BD Biosciences) and the FlowJo program (Tree Star, San Carlos, CA, U.S.A.).

2. Results

Figure 19:
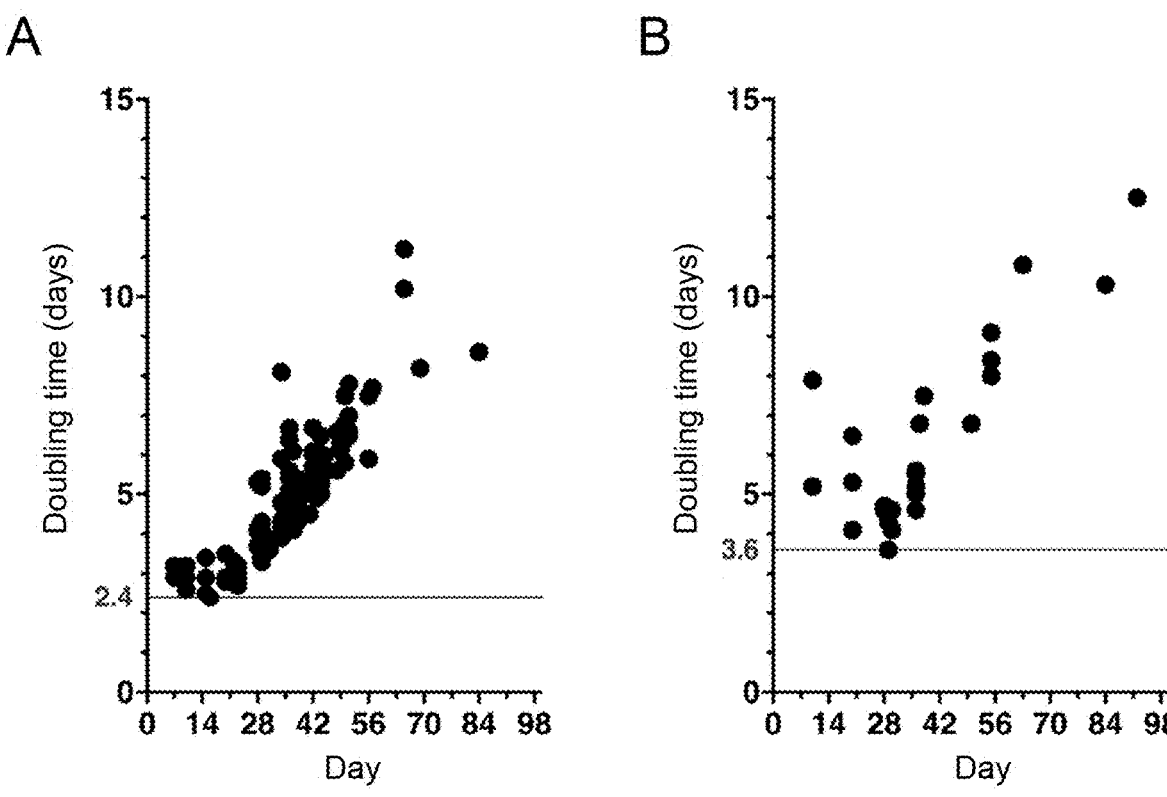
FIG. 19 shows the human liver cell doubling time in the TK-NOG-IL-6 mice (A) and in the TK-NOG mice (B).

FIG. 19A shows the results of measurement of the doubling time of human liver cells transplanted into TK-NOG-IL-6 mice and FIG. 19B shows the results of measurement of the doubling time of human liver cells transplanted into TK-NOG mice.

The minimal doubling time of human liver cells transplanted into TK-NOG-IL-6 mice was 2.4 days, and the minimal doubling time of human liver cells transplanted into TK-NOG mice was 3.6 days. This demonstrates that use of TK-NOG-IL-6 mice would increase the human liver cell growth rate by approximately 1.5 times.

In this example, immunodeficient mice are used as non-human vertebrates. From the viewpoint of the mechanism of human liver cell engraftment, it can be deduced that effects of human IL-6 can be exerted with the use of immunodeficient non-human vertebrates other than mice, as with the use of mice.

[Example 3] Influence of Anti-IL-6 Neutralizing Antibody on Human Liver Cell Growth in TK-NOG-IL-6 Mice As described in Example 1, human IL-6 was effective for the growth of human liver cells in mammals other than humans, and the growth rate of the human liver cells transplanted into TK-NOG-IL-6 mice was increased.

There is a report such that, "the anti-cytokine antibody serves as a cytokine carrier protein in vivo and functions for a long period of time by protecting human IL-6 from degradation" (FD Finkelman et al., J. Immunol., Aug. 1, 1993, 151 (3), 1993, pp. 1235-44: May LT. et al., J. Immunol., Sep. 15, 1993, 151 (6), pp. 3225-36). Accordingly, whether or not effects of human IL-6 could be enhanced via transplantation of human liver cells into TK-NOG-IL-6 mice, followed by administration of a neutralizing antibody against human IL-6, was examined.

1. Materials and Method (1) Induction of Liver Injury and Transplantation of Human Liver Cells As described in Example 1, ganciclovir was administered to TK-NOG-IL-6 mice, blood samples were collected in heparin 1 week after administration, blood plasma was separated therefrom, and clinical chemical analysis (alanine amino transferase; ALT) was then performed using FUJI DRI-CHEM7000 (Fujifilm).

Commercially available frozen human liver cells (Lonza, 11-month-old, HUM4282) were used as donor cells. The donor cells were transplanted into TK-NOG-IL-6 in the manner described below. Adult TK-NOG-IL-6 recipient mice (6- to 8-week-old) were allowed to drink a ValGCV solution (0.27 mg/ml) for 72 hours, blood samples were collected 1 week after the initiation of administration, and plasma ALT levels were then measured. Mice with the plasma ALT value of 300 U/1 or higher were designated as recipient mice of human liver cell transplantation. The human liver cell count and the viability thereof were determined using a hematocytometer by the trypan blue exclusion method. Viable liver cells (approximately $1×10^6$ cells) floated in 40 µl of William's E medium were administered to the spleens using a glass syringe with a 29-gauge needle for subcutaneous insulin administration (Myjector).

(2) Separation of the Group to which the Anti-Human IL-6 Antibody is Administered from the Group to which No Anti-Human IL-6 Antibody is Administered Mice were arranged in descending order of ALT activity measured before transplantation of human liver cells, mice were alternately divided into two groups (each group consisting of 4 female mice), and a significant difference test (Mann-Whitney test) was performed to confirm that there was no difference between two groups in terms of the average ALT activity. In addition, it was confirmed that there was no significant difference between these two groups in terms of the average body weight before antibody administration (Mann-Whitney test). An arbitrarily selected group was designated to be the group to which the antibody was administered.

(3) Schedule for Administration of Anti-Human IL-6 Antibody and Blood Sampling

The anti-human IL-6 antibody (a mixture of equal amounts of 2 types of antibodies: 2 µg of Sino Biological IL6/IL-6 Neutralizing Antibody, Clone mhk23 and 2 µg of Invitrogen IL-6 Antibody, Monoclonal, 505E9A12A3) was administered subcutaneously to mice on Tuesday on the next week after human liver cell transplantation in an amount of 4 µg per mouse once a day for 4 consecutive days (Tuesday, Wednesday, Thursday, and Friday), drug administration was suspended for 2 days (Saturday and Sunday), the drug was administered subcutaneously at the same dose for 5 consecutive days (Monday, Tuesday, Wednesday, Thursday, and Friday), drug administration was suspended for 2 days (Saturday and Sunday), the drug was administered subcutaneously at the same dose for 5 consecutive days (Monday, Tuesday, Wednesday, Thursday, and Friday), drug administration was suspended for 2 days (Saturday and Sunday), and the drug was then administered subcutaneously at the same dose once (Monday) (15 times in total). Blood sampling was performed on every Tuesday starting from 2 weeks after transplantation to 5 weeks after transplantation.

(4) Measurement of Human Albumin

A small amount of blood was collected from the venous plexus on the ocular fundus using a polyethylene tube, and blood plasma was separated therefrom. The blood plasma was diluted to 5,000- to 250,000-fold using tris-buffered saline (TBS) containing 1% bovine serum albumin/0.05% Tween 20, and human albumin concentration was measured using the human albumin ELISA Quantitation Kit (Bethyl Laboratories).

(5) Measurement of Cholinesterase Activity

A small amount of blood was collected from the venous plexus on the ocular fundus using a polyethylene tube, and blood plasma was separated therefrom. The blood plasma was subjected to clinical chemical analysis (cholinesterase; CHE) using FUJI DRI-CHEM7000 (Fujifilm). The mouse blood plasma has substantially no cholinesterase activity. Accordingly, cholinesterase activity detected is derived from human liver cells, the enzymatic activity is highly correlated with human albumin concentration, and cholinesterase activity is thus reported to serve as a human liver cell engraftment marker as an alternative to human albumin (Suemizu et al., 2018, Pest Manage Sci., 74, 1424-1430).

2. Results

Figure 20:
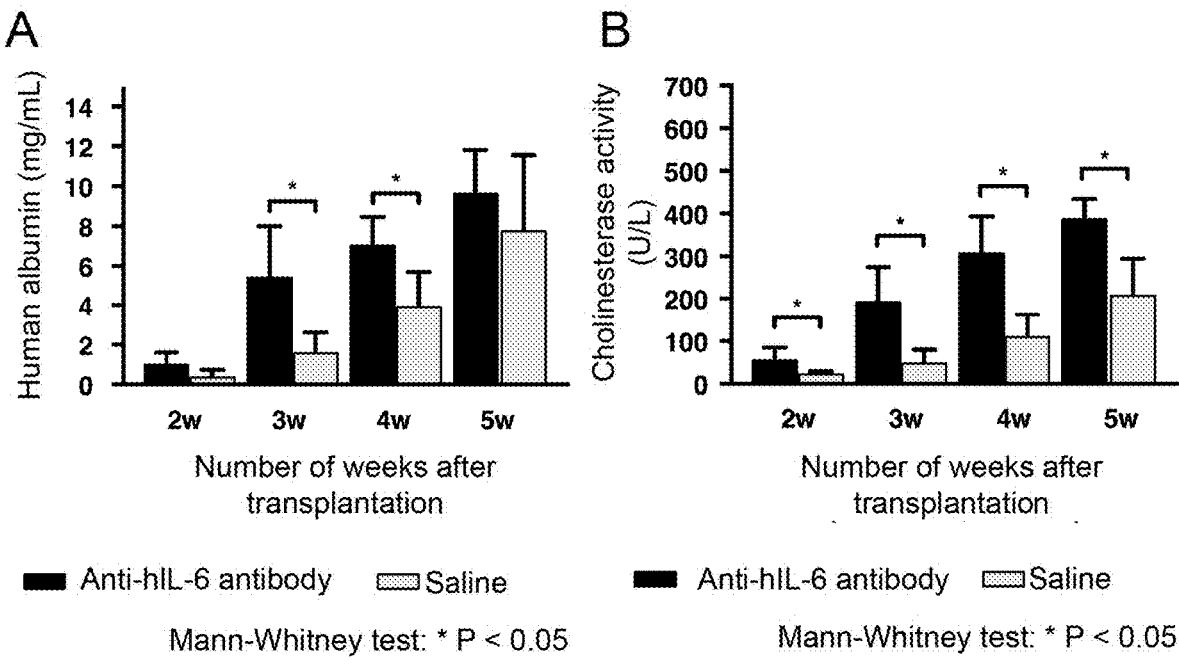
FIG. 20 shows the results of measurement of human serum albumin concentration (A) and cholinesterase activity (B) in the blood, when the anti-IL-6 antibody is administered to the TK-NOG-IL-6 mice following transplantation of human liver cells.

FIG. 20A shows the results of measurement of human albumin concentration in the blood, and FIG. 20B shows the results of measurement of cholinesterase activity.

As shown in FIG. 20A, the group to which the human anti-IL-6 antibody had been administered exhibited higher human albumin levels than the group to which no antibody had been administered during a period from 2 weeks to 5 weeks after transplantation of human liver cells. In particular, the human albumin levels measured 3 weeks and 4 weeks after transplantation of human liver cells were high with a statistically significant difference. As shown in FIG. 20B, the group to which the human anti-IL-6 antibody had been administered exhibited higher cholinesterase activity than the group to which no antibody had been administered with a statistically significant difference throughout the period from 2 weeks to 5 weeks after transplantation of human liver cells. This indicates that administration of the human anti-IL-6 antibody would accelerate engraftment and growth of the transplanted human liver cells.

INDUSTRIAL APPLICABILITY

The non-human vertebrate of the present invention comprises liver cells replaced with human liver cells, and it has a structure or functions of the human liver. Use of the non-human vertebrate of the present invention enables development of a drug used for human liver diseases and collection of human liver cells.

All publications, patents, and patent applications cited herein are incorporated herein by reference in their entirety.

The invention claimed is:

1. A method for producing a transgenic immunodeficient mouse expressing a human Interleukin-6 (hIL-6) transgene and comprising human liver cells transplanted therein, the method comprising:

providing an immunodeficient mouse expressing hIL-6 wherein the somatic and germ cells of the immunodeficient mouse comprise a constitutively-active transgene encoding hIL-6 and the endogenous mouse IL-6 gene is not disrupted;

inducing liver injury in the immunodeficient mouse expressing the hIL-6 transgene; and transplanting human liver cells into the liver of the immunodeficient mouse expressing the hIL-6 transgene, wherein 70% or more mouse liver cells are replaced with human liver cells such that human liver tissue is produced that comprises a portal triad composed of an interlobular artery, interlobular vein, and interlobular bile duct and functions of the human liver, and the liver injury is induced by one or more of the methods selected from the group consisting of (i) to (iv):

(i) administering a suicide substrate to the immunodeficient mouse expressing the hIL-6 transgene, wherein the liver cells of the immunodeficient mouse expressing the hIL-6 transgene express thymidine kinase, and wherein the suicide substrate is a guanosine analog;

(ii) expressing a urokinase-type plasminogen activator gene in the liver cells of the immunodeficient mouse expressing the hIL-6 transgene;

(iii) impairing the fumarylacetoacetate hydrolase (Fah) gene of the immunodeficient mouse expressing the hIL-6 transgene; and (iv) administering any of the compounds (a) to (e) below: (a) carbon tetrachloride; (b) acetaminophen; (c) d-galactosamine; (d) thioacetamide; and (e) anti-Fas antibody.

2. The method according to claim 1, wherein the immunodeficient mouse is a TK-NOG mouse prepared by:

(i) microinjecting a human herpes simplex virus type 1-thymidine kinase (HSV-tk) gene into a fertilized egg of a NOD/Shi mouse;

(ii) generating a NOD/Shi mouse having the HSV-tk gene from the fertilized egg of step (i); and (iii) mating the NOD/Shi mouse having the HSV-tk gene obtained in step (ii) with a NOG (NOD/SCID/yc$^{null}$) mouse.

3. The method according to claim 2, wherein the liver injury is induced by administering a suicide substrate to the TK-NOG mouse expressing the hIL-6 transgene.

4. The method according to claim 1, wherein the immunodeficient mouse expressing the hIL-6 transgene is a TK-NOG-IL-6 mouse obtained by:

(i) microinjecting a DNA fragment comprising human IL-6 cDNA into a fertilized egg obtained by mating a female NOD mouse and a male NOG mouse to obtain a human IL-6 transgenic founder mouse;

(ii) mating the human IL-6 transgenic founder mouse obtained in (i) with a NOG mouse to obtain a scid-IL2Rg$^{null}$ mutant to obtain a NOG-IL-6 mouse; and (iii) mating the NOG-IL-6 mouse obtained in step (ii) with a TK-NOG mouse.

5. The method according to claim 1, wherein the human liver cell is a primary human hepatocyte.

6. The method according to claim 1, wherein the thymidine kinase is encoded by a human herpes simplex virus type 1-thymidine kinase (HSV-tk) gene positioned under the control of a liver-specific promoter selected from an albumin promoter, a transthyretin promoter, a thyroxine binding globulin promoter, an LST-1 promoter, an α-fetoprotein promoter, or an α-TTP promoter.

7. The method according to claim 1, wherein the liver injury is induced by the combination of the method (iv) and any of the methods (i) to (iii).

8. The method according to claim 1, wherein the growth rate of the transplanted human liver cells is at least 1.5 times higher than the growth rate of the transplanted human liver cells in an immunodeficient mouse in which human IL-6 is not present.

9. The method according to claim 1, further comprising administering a human anti-IL-6 antibody, following transplantation of human liver cells.

10. The mouse produced by the method of claim 1, wherein the mouse is a immunodeficient mouse expressing hIL-6 and human liver cells transplanted therein, wherein the mouse has a liver injury, and wherein the immunodeficient mouse expressing hIL-6 comprises a constitutively-active transgene encoding hIL-6 in the somatic and germ cells and the endogenous mouse IL-6 gene is not disrupted.

* * * * *